US011712391B2

(12) United States Patent
Otsuki et al.

(10) Patent No.: US 11,712,391 B2
(45) Date of Patent: Aug. 1, 2023

(54) STATE ESTIMATION PROGRAM, TRAINED MODEL, REHABILITATION SUPPORT SYSTEM, LEARNING APPARATUS, AND STATE ESTIMATION METHOD

(71) Applicant: TOYOTA JIDOSHA KABUSHIKI KAISHA, Toyota (JP)

(72) Inventors: Nobuhisa Otsuki, Toyota (JP); Issei Nakashima, Toyota (JP); Manabu Yamamoto, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 487 days.

(21) Appl. No.: 16/918,107

(22) Filed: Jul. 1, 2020

(65) Prior Publication Data
US 2021/0000677 A1  Jan. 7, 2021

(30) Foreign Application Priority Data

Jul. 1, 2019  (JP) .................................. 2019-123128

(51) Int. Cl.
*A61H 1/02* (2006.01)
*G16H 20/30* (2018.01)
(Continued)

(52) U.S. Cl.
CPC ......... *A61H 1/0229* (2013.01); *A61H 1/0262* (2013.01); *G06N 20/00* (2019.01);
(Continued)

(58) Field of Classification Search
CPC ...... A61H 3/008; A61H 1/024; A61H 1/0229; A61H 2003/007; A61H 1/0255; A61H 2201/12; A61H 2201/1652; A61H 2201/164; A61H 3/00; A61H 1/0262; A61H 2201/1215; A61H 2201/5071; A61H 2201/1207; A61H 2201/5043; A61H 2201/5069; A61H 2201/50; A61H 2201/5058; A61H 2201/5061;
(Continued)

(56) References Cited

U.S. PATENT DOCUMENTS 4,620,703 A * 11/1986 Greenhut ............. A63B 21/153
482/901
4,635,875 A *  1/1987 Apple ................... B66D 1/741
254/294
(Continued)

FOREIGN PATENT DOCUMENTS

JP   2015-223294 A   12/2015

*Primary Examiner* — Garrett K Atkinson
(74) *Attorney, Agent, or Firm* — Oliff PLC

(57) ABSTRACT

A state estimation program is for causing a computer to function to determine a state of training in a rehabilitation support system used by a trainee to perform training of a preset motion and includes a threshold setting step and a state estimation step. The threshold setting step is for acquiring a sensor output, the sensor output being an output of a sensor included in the rehabilitation support system in the training performed by the trainee and setting a threshold for determining one of a normal state and an abnormal state of the training based on the sensor output. The state estimation step is for estimating whether the training is performed in the normal state or the abnormal state based on the threshold.

10 Claims, 20 Drawing Sheets

(51) Int. Cl.
*G06N 20/00* (2019.01)
*G06V 40/20* (2022.01)
*G06V 10/764* (2022.01)
*G06V 10/82* (2022.01)

(52) U.S. Cl.
CPC ............ *G06V 10/764* (2022.01); *G06V 10/82* (2022.01); *G06V 40/25* (2022.01); *G16H 20/30* (2018.01); *A61H 2201/1215* (2013.01); *A61H 2201/5071* (2013.01)

(58) Field of Classification Search
CPC .... A61H 2201/5084; A61H 2201/5097; A61H 2203/0406; A61H 2205/10; A61H 2230/625; A61H 2003/005; A61H 2201/1642; A61H 2201/165; A61H 2201/5079; B66D 1/505; B66D 1/12; B66D 1/36; B66D 1/28; A63B 21/153; A63B 24/0087; A63B 22/0235; A63B 21/00181; G06N 20/00; G06N 3/084; G06N 3/0445; G06V 40/25; G06V 10/764; G06V 10/82; G16H 20/30; G16H 40/63

See application file for complete search history.

(56) References Cited

U.S. PATENT DOCUMENTS

| | | | | |
|---|---|---|---|---|
| 4,724,827 A * | 2/1988 | Schenck | ............. | A61H 1/0288 601/40 |
| 5,667,461 A * | 9/1997 | Hall | ................... | A63B 69/0064 482/54 |
| 6,123,649 A * | 9/2000 | Lee | ................... | A63B 21/4013 482/54 |
| 6,666,831 B1 * | 12/2003 | Edgerton | .......... | A63B 69/0064 600/595 |
| 6,796,926 B2 * | 9/2004 | Reinkensmeyer | ..... | A61H 3/008 482/8 |
| 7,331,906 B2 * | 2/2008 | He | ...................... | A61H 1/0237 482/69 |
| 7,494,450 B2 * | 2/2009 | Solomon | .......... | A63B 21/00181 482/69 |
| 7,887,471 B2 * | 2/2011 | McSorley | .......... | A63B 21/0552 482/136 |
| 7,998,040 B2 * | 8/2011 | Kram | ................... | A63B 21/055 482/54 |
| 8,057,410 B2 * | 11/2011 | Angold | .................... | A61H 3/00 601/5 |
| 8,608,479 B2 * | 12/2013 | Liu | ......................... | A61H 3/04 434/255 |
| 9,638,163 B2 * | 5/2017 | Holloway | ............... | B66C 13/08 |
| 9,737,453 B2 * | 8/2017 | Shimada | ........... | A63B 22/0046 |
| 10,465,663 B2 * | 11/2019 | Holloway | ............... | B66C 13/08 |
| 10,825,318 B1 * | 11/2020 | Williams | ............... | G16H 80/00 |
| 2003/0064869 A1 * | 4/2003 | Reinkensmeyer | ..... | A61H 3/008 482/8 |
| 2004/0087418 A1 * | 5/2004 | Eldridge | ........... | A63B 69/0022 482/54 |
| 2004/0204294 A2 * | 10/2004 | Wilkinson | ........... | A63B 22/203 482/52 |
| 2005/0101448 A1 * | 5/2005 | He | ....................... | A61H 1/0255 482/69 |
| 2008/0300118 A1 * | 12/2008 | Wehrell | ............... | A63B 21/169 482/129 |
| 2012/0004581 A1 * | 1/2012 | Dinon | .................. | A61H 1/0237 601/23 |
| 2013/0130866 A1 * | 5/2013 | Wehrell | ............. | A63B 69/0079 482/112 |
| 2013/0184128 A1 * | 7/2013 | Towley, III | ........ | A63B 23/0355 482/102 |
| 2013/0225371 A1 * | 8/2013 | Harrer | ................ | A63B 21/0552 482/8 |
| 2014/0121071 A1 * | 5/2014 | Strom | ................. | A63B 21/156 482/99 |
| 2015/0232307 A1 * | 8/2015 | Holloway | ............... | B66C 13/08 254/338 |
| 2015/0342820 A1 * | 12/2015 | Shimada | ............ | A63B 22/0087 482/69 |
| 2017/0218927 A1 * | 8/2017 | Holloway | ............... | F03D 80/50 |
| 2019/0282131 A1 * | 9/2019 | Chang | ..................... | B25J 9/163 |
| 2019/0283247 A1 * | 9/2019 | Chang | .................... | G05B 17/02 |
| 2021/0043058 A1 * | 2/2021 | Williams | ................ | G06N 3/08 |

* cited by examiner

STATE ESTIMATION PROGRAM, TRAINED MODEL, REHABILITATION SUPPORT SYSTEM, LEARNING APPARATUS, AND STATE ESTIMATION METHOD

CROSS REFERENCE TO RELATED APPLICATIONS

This application is based upon and claims the benefit of priority from Japanese patent application No. 2019-123128, filed on Jul. 1, 2019, the disclosure of which is incorporated herein in its entirety by reference.

BACKGROUND

The present disclosure relates to a state estimation program, a trained model, a rehabilitation support system, a learning apparatus, and a state estimation method.

A patient suffering from hemiplegia or the like may use a rehabilitation support system such as a walking training apparatus when performing rehabilitation for the purpose of relieving bad conditions. As an example of a walking training apparatus, a walking training apparatus including a walking assistance apparatus attached to a patient's leg who is a trainee to assist him/her to walk is disclosed (Japanese Unexamined Patent Application Publication No. 2015-223294). The walking training apparatus includes a treadmill or the like for making the trainee walk. The walking assistance apparatus includes a motor unit and assists the trainee to walk by rotationally driving his/her knee joint according to a walking motion of the trainee.

In some rehabilitation support systems, when a trainee performs rehabilitation, a trainee is accompanied by a training staff member such as a doctor or physical therapist (PT) to assist the trainee in setting up the rehabilitation support system.

SUMMARY

In training using such a rehabilitation support system, there is a case in which training is not performed normally, i.e., an abnormal state occurs. An example of the abnormal state is when a trainee under training exhibits an unexpected behavior such as falling down suddenly. Another example of the abnormal state is when the rehabilitation support system is configured with a setting that does not fit for a purpose of the training, such as forcing the trainee to walk regardless of the trainee's symptoms. The rehabilitation support system is required to ensure the trainee's safety in such unexpected situations. Thus, the training staff member supports the trainee's body and performs operations to stop the operation of the rehabilitation support system urgently. However, it is difficult for a training staff member to perform a plurality of such operations at the same time.

The present disclosure has been made to solve such a problem. An object of the present disclosure is to provide a state estimation program and the like for effectively preventing lowering of a trainee's safety.

An example aspect of the present disclosure is a state estimation program for causing a computer to function to determine a state of training in a rehabilitation support system used by a trainee to perform training of a preset motion and includes a threshold setting step and a state estimation step. The threshold setting step is for acquiring a sensor output, the sensor output being an output of a sensor included in the rehabilitation support system in the training performed by the trainee and setting a threshold for determining one of a normal state and an abnormal state of the training based on the sensor output. The state estimation step is for estimating whether the training is performed in the normal state or the abnormal state based on the threshold.

Thus, the state estimation program sets a threshold for estimating whether the training is in the normal state or the abnormal state from the sensor output of the training performed in advance, and estimates the state of the training during the training according to the set threshold.

In the above state estimation program, the threshold setting step may further include acquiring profile data of the trainee in addition to the sensor output and setting the threshold based on the sensor output and the profile data. Thus, the state estimation program can set the threshold according to the profile data of the trainee.

In the above state estimation program, the acquiring step may include acquiring the sensor output including data related to a walking cycle of the trainee, and the threshold setting step may include setting the threshold corresponding to the walking cycle. Thus, the state estimation program can set the threshold corresponding to the cycle of the walking training, and estimate whether the walking training is in the normal state or the abnormal state.

In the above state estimation program, the output of the sensor may include data acquired by detecting a walking posture of the trainee. Thus, the state estimation program can set the threshold corresponding to the walking posture of the trainee.

Another example aspect of the present disclosure is a trained model for causing a computer to function to determine a state of training in a rehabilitation support system used for a trainee to perform training of a preset motion. The trained model includes: an input layer configured to acquire a sensor output, the sensor output being an output of a sensor included in the rehabilitation support system, an intermediate layer configured to perform a calculation based on the sensor output acquired by the input layer, and an output layer configured to output a result of the calculation. The intermediate layer is learned by applying, to the output layer, an index indicating whether the training corresponding to the sensor output acquired by the input layer as learning data is the normal state or the abnormal state as teacher data. In the above trained model, when the sensor output in the rehabilitation support system under training is input to the input layer, a state signal indicating whether the training is the normal state or the abnormal state is output.

Thus, the trained model can estimate whether the training is in the normal state or the abnormal state from the sensor output acquired in advance.

In the above trained model, the input layer may be configured to further acquire profile data of the trainee, and the intermediate layer may be configured to determine the state of the trainee based on the sensor output and the profile data. Thus, the trained model can determine the state of the training according to the profile data of the trainee.

In the above trained model, the input layer may be configured to acquire the sensor output including data related to a walking cycle of the trainee, and the intermediate layer may be configured to estimate a state of the rehabilitation support system corresponding to the walking cycle. Thus, the trained model can estimate whether the walking training is in the normal state or the abnormal state.

In the above trained model, the output of the sensor may include data acquired by detecting a walking posture of the trainee. Thus, the trained model can perform estimation corresponding to the walking posture of the trainee.

Another example aspect of the present disclosure is a rehabilitation support system including a drive unit, a sensor, a state estimation unit, and an information presentation unit. The drive unit is configured to be driven to correspond to a motion of the trainee in order to support the motion of the trainee. The sensor is configured to detect at least one of a state of the trainee and a state of the drive unit. The state estimation unit is configured to include any one of the above-described state estimation programs and to estimate whether the training performed by the trainee is the normal state or the abnormal state by acquiring the sensor output. The information presentation unit is configured to present whether or not the training is in the abnormal state to the trainee or a training staff member assisting the trainee based on the state signal output by the control unit. Thus, the rehabilitation support system can present a state of training to the trainee and the like according to the signal acquired from the state estimation program.

Another example aspect of the present disclosure is a rehabilitation support system including a drive unit, a sensor, a calculation unit, and an information presentation unit. The drive unit is configured to be driven to correspond to a motion of the trainee in order to support the motion of the trainee. The sensor is configured to detect at least one of a state of the trainee and a state of the drive unit. The calculation unit is configured to include any one of the above-described trained models and to output a state estimation signal for estimating whether the training performed by the trainee is the normal state or the abnormal state by acquiring the sensor output. The information presentation unit is configured to present whether or not the training is in the abnormal state to the trainee or a training staff member assisting the trainee based on the state estimation signal output by the calculation unit. Thus, the rehabilitation support system can present a state of training to the trainee and the like according to the signal acquired from the trained model.

The above rehabilitation support system further includes a drive control unit configured to control the drive unit, and the drive control unit may be configured to stop the drive of the drive unit when the training is estimated to be the abnormal state. Thus, the rehabilitation support system can effectively prevent lowering of the trainee's safety.

In the above rehabilitation support system, the drive control unit may be configured to, when the drive of the drive unit is stopped, decelerate a driving speed of the drive unit and then stop the drive of the drive unit. Further, in the above rehabilitation support system, the drive control unit may be configured to stop the drive of the drive unit and then drive the drive unit in a direction opposite to a driving direction right before the drive unit is stopped. Thus, the rehabilitation support system can more effectively prevent lowering of the trainee's safety.

Another example aspect of the present disclosure is a learning apparatus that includes a data acquisition unit, a learning unit, and a trained model generation unit. The data acquisition unit is configured to acquire an output of a sensor included in a rehabilitation support system used by a trainee to perform training of a preset motion and a state label as learning data, the state label indicating whether a state of the training corresponding to the output of the sensor is a normal state or an abnormal state. The learning unit is configured to learn by applying the output of the senor to an input layer and applying the state label corresponding to the output of the sensor to an output layer as teacher data to thereby determine whether the state of the training is the normal state or the abnormal state. The trained model generation unit is configured to generate a trained model, the trained model receiving the output of the sensor related to the trained model that has not been learned yet and outputting a state signal indicating that the state of the training is one of the normal state and the abnormal state based on the learning. Thus, the learning apparatus can generate a trained model for preventing lowering of the trainee's safety.

According to the present disclosure, it is possible to provide a state estimation program and the like for effectively preventing lowering of a trainee's safety.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Hereinafter, the present disclosure will be explained through embodiments of the present disclosure. However, they are not intended to limit the scope of the present disclosure according to the claims. Note that the same elements are denoted by the same reference signs throughout the drawings, and repeated description is omitted as necessary. Note that the same elements are denoted by the same reference signs throughout the drawings, and repeated description is omitted as necessary.

First Embodiment

Figure 1:
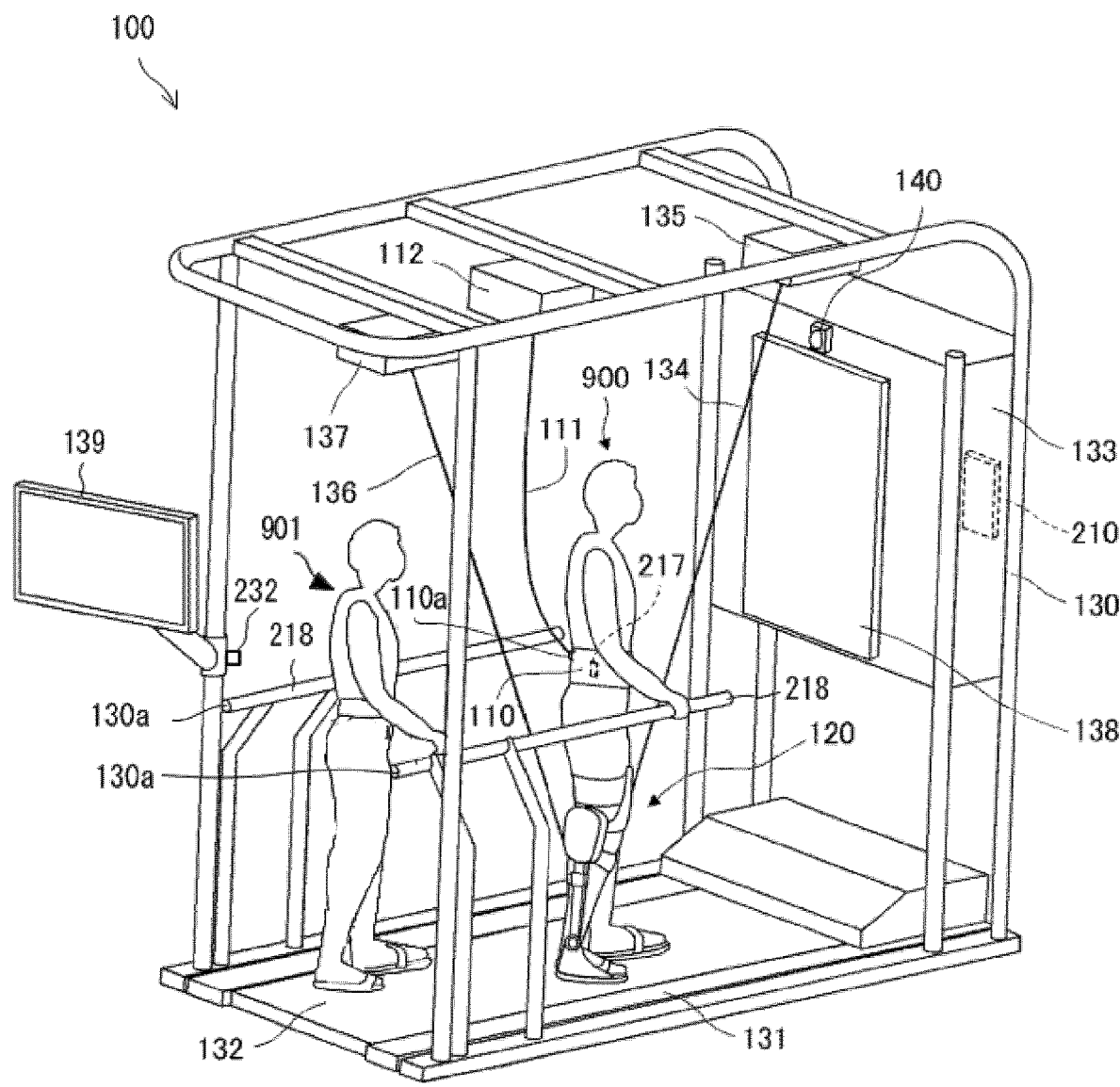
FIG. 1 is a schematic perspective view of a walking training apparatus according to a first embodiment.

A first embodiment will be described hereinafter with reference to the drawings.
(System Configuration)
FIG. 1 is a schematic perspective view of a walking training apparatus 100 according to a first embodiment. The walking training apparatus 100 is a specific example of a rehabilitation support system that supports rehabilitation performed by a trainee 900 who is a user. The walking training apparatus 100 is an apparatus by which the trainee 900, who is, for example, a hemiplegic patient suffering from paralysis in one of his/her legs, does walking training under the guidance of a training staff member 901. When walking training is performed, the walking training apparatus 100 drives a drive unit that is driven according to the trainee's motion in order to support the trainee's motion. Note that the training staff member 901 can be a therapist (a physical therapist) or a doctor, and may also be referred to as a training instructor, a training assistant, a training supporter, or the like because he/she instructs the trainee in training or assists the trainee by giving assistance and the like.

The walking training apparatus 100 mainly includes a control panel 133 attached to a frame 130 forming an overall framework, a treadmill 131 on which the trainee 900 walks, and a walking assistance apparatus 120 attached to the diseased leg, i.e., the leg on the paralyzed side of the trainee 900. In addition to these components, the walking training apparatus 100 further includes a fall-prevention harness apparatus as a safety apparatus.

The treadmill 131 is an apparatus that prompts the trainee 900 to walk. The treadmill 131 rotates a ring-shaped belt 132 by using a motor (not shown). The trainee 900, who does a walking training, gets on the belt 132 and tries walking in accordance with the movement of the belt 132. That is, the treadmill 131 is one of the drive units that are driven according to the trainee's motion in order to support the trainee's motion. Note that the training staff member 901 can stand on the belt 132 behind the trainee 900 and walk together as shown in FIG. 1. However, the training staff member 901 may typically be in a state in which he/she can easily assists the trainee 900 such as standing with his/her feet on both sides of the belt 132.

The frame 130 is disposed in a standing position on the treadmill 131 mounted on the floor surface. The frame 130 supports, for example, the control panel 133 that houses an overall control unit 210 that controls motors and sensors, and a training monitor 138 that is formed by, for example, a liquid-crystal panel and shows progress of the training and the like to the trainee 900. Further, the frame 130 supports a front pulling unit 135 roughly above and in front of the head of the trainee 900, supports a harness pulling unit 112 roughly above the head, and supports a rear pulling unit 137 roughly above and behind the head. Further, the frame 130 also includes handrails 130a that the trainee 900 grasps.

The handrails 130a are disposed on the left and right sides of the trainee 900. Each of the handrails 130a is orientated in a direction parallel to the walking direction of the trainee 900. The vertical position and the left/right position of the handrails 130a are adjustable. That is, the handrails 130a may include a mechanism for changing its height. Further, the handrails 130a can be configured so that their inclination angles can be changed by, for example, adjusting the heights of their front sides and the rear sides in the walking direction to different heights. For example, the handrails 130a can have an inclination angle so that their heights gradually increase along the walking direction.

Further, each of the handrails 130a is equipped with a handrail sensor 218 that detects a load (e.g., a pressure) received from the trainee 900. For example, the handrail sensor 218 may be a resistance change detection-type load detection sheet in which electrodes are arranged in a matrix pattern. Further, the handrail sensor 218 may be a six-axis sensor in which a three-axis acceleration sensor (x, y, z) is combined with a three-axis gyro sensor (roll, pitch, yaw). However, there is no particular limitation on the type of the handrail sensor 218 and the place where the handrail sensor 218 is disposed.

The camera 140 functions as an image pickup unit for observing the whole body of the trainee 900. The camera 140 is disposed near the training monitor 138 and positioned so as to face the trainee. The camera 140 takes still images and moving images of the trainee 900 during the training. The camera 140 includes a set of a lens and an image pickup device so that it has such an angle of view that it can shoot the whole body of the trainee 900. The image pickup device is, for example, a CMOS (Complementary Metal-Oxide-Semiconductor) image sensor, and converts an optical image formed on an image forming surface into an image signal.

The training monitor 138 is a display device provided as an information presentation unit for the trainee 900 and the training staff member 901 to acquire predetermined information during training. The training monitor 138 is installed so as to face the front of the trainee during training. The training monitor 138 displays, for example, an image of the trainee 900 during training captured by, for example, the camera 140. The training monitor 138, as an information presenting unit, may present to the trainee 900 and the training staff member 901 whether the training being performed is in an abnormal state, in accordance with a state signal output by the overall control unit 210.

By the coordinated operation of the front pulling unit 135 and the rear pulling unit 137, the load of the walking assistance apparatus 120 is cancelled so that it does not become a load on the diseased leg. Further, the swinging motion of the diseased leg is assisted according to the set level. That is, the front pulling unit 135 and the rear pulling unit 137 are one of the drive units that are driven according to the trainee's motion in order to support the trainee's motion.

One end of a front wire 134 is connected to a winding mechanism of the front pulling unit 135 and the other end thereof is connected to the walking assistance apparatus 120. The winding mechanism of the front pulling unit 135 winds or pays out the front wire 134 according to the motion of the diseased leg by turning on/off a motor (not shown). Similarly, one end of a rear wire 136 is connected to the winding mechanism of the rear pulling unit 137 and the other end thereof is connected to the walking assistance apparatus 120. The winding mechanism of the rear pulling unit 137 winds or pays out the rear wire 136 according to the motion of the diseased leg by turning on/off a motor (not shown). By the coordinated operation of the front pulling unit 135 and the rear pulling unit 137 as described above, the load of the walking assistance apparatus 120 is cancelled so that it does not become a load on the diseased leg. Further, the swinging motion of the diseased leg is assisted according to the set level.

For example, the training staff member 901, who serves as an operator, increases the set assistance level for a trainee who suffers from severe paralysis. When the assistance level is set to a large value, the front pulling unit 135 winds the front wire 134 with a relatively large force according to the timing of the swinging of the diseased leg. When the training has progressed and the assistance is no longer required, the training staff member 901 sets the assistance level to the minimum value. When the assistance level is set to the minimum value, the front pulling unit 135 winds the front wire 134 according to the timing of the swinging of the diseased leg with a force by which only the weight of the walking assistance apparatus 120 itself is cancelled.

The fall-prevention harness apparatus includes, as its main components, a harness 110, a harness wire 111, and a harness pulling unit 112. The harness 110 is a belt that is wound around the abdomen of the trainee 900 and is fixed to his/her waist by, for example, a hook-and-loop fastener. The harness 110 includes a connection hook 110a that connects one end of the harness wire 111, which serves as a hoisting tool, to the harness 110, and may be referred to as a hanger belt. The trainee 900 attaches the harness 110 to his/her diseased leg so that the connection hook 110a is positioned in the rear part of the diseased leg.

One end of the harness wire 111 is connected to the connection hook 110a of the harness 110 and the other end thereof is connected to a winding mechanism of the harness pulling unit 112. The winding mechanism of the harness pulling unit 112 winds or pays out the harness wire 111 by turning on/off a motor (not shown). By the above-described configuration, when the trainee 900 is about to fall down, the fall-prevention harness apparatus winds the harness wire 111 according to an instruction from the overall control unit 210, which has detected the falling-down movement of the trainee 900, and thereby supports the upper body of the trainee 900 by the harness 110, so that the trainee 900 is prevented from falling down.

The harness 110 includes a posture sensor 217 for detecting the posture of trainee 900. The posture sensor 217 is, for example, a combination of a gyro sensor and an acceleration sensor, and outputs an inclination angle of the abdomen, to which the harness 110 is attached, with respect to the direction of gravity.

A management monitor 139 is attached to the frame 130 and serves as a display/input device by which the training staff member 901 or the like monitors and operates the rehabilitation support system. The management monitor 139 is formed by, for example, a liquid crystal panel. Further, a touch panel is disposed over its surface. The management monitor 139 displays various menu items related to the training setting, various parameter values during the training, training results, and so on. The management monitor 139, as an information presenting unit, may present to the training staff member 901 whether the training being performed is in an abnormal state, in accordance with a state signal output by the overall control unit 210.

An emergency stop button 232 is a button for urgently stopping the treadmill 131, the front pulling unit 135, and the rear pulling unit 137 when an emergency such as a trainee falls down occurs during training. The emergency stop button 232 is provided at a position where the training staff member 901 can instantly press it.

The walking assistance apparatus 120 is attached to the diseased leg of the trainee 900 and assists the trainee 900 in walking by reducing the load of the extension and flexion at the knee joint of the diseased leg. The walking assistance apparatus 120 includes a sensor or the like that measures the load (e.g., the pressure) on the sole of the foot, and outputs various data related to the moving leg to the overall control unit 210. Further, the harness 110 can be connected to the walking assistance apparatus 120 by using a connection member (hereinafter referred to as a hip joint) including a rotation part. Details of the walking assistance apparatus 120 will be described later.

In this embodiment, the terms "leg" and "leg part" are used to refer to the entire part of the leg below the hip joint, and the terms "foot" and "foot part" are used to refer to a part of the leg from the ankle to the toe.

Figure 2:
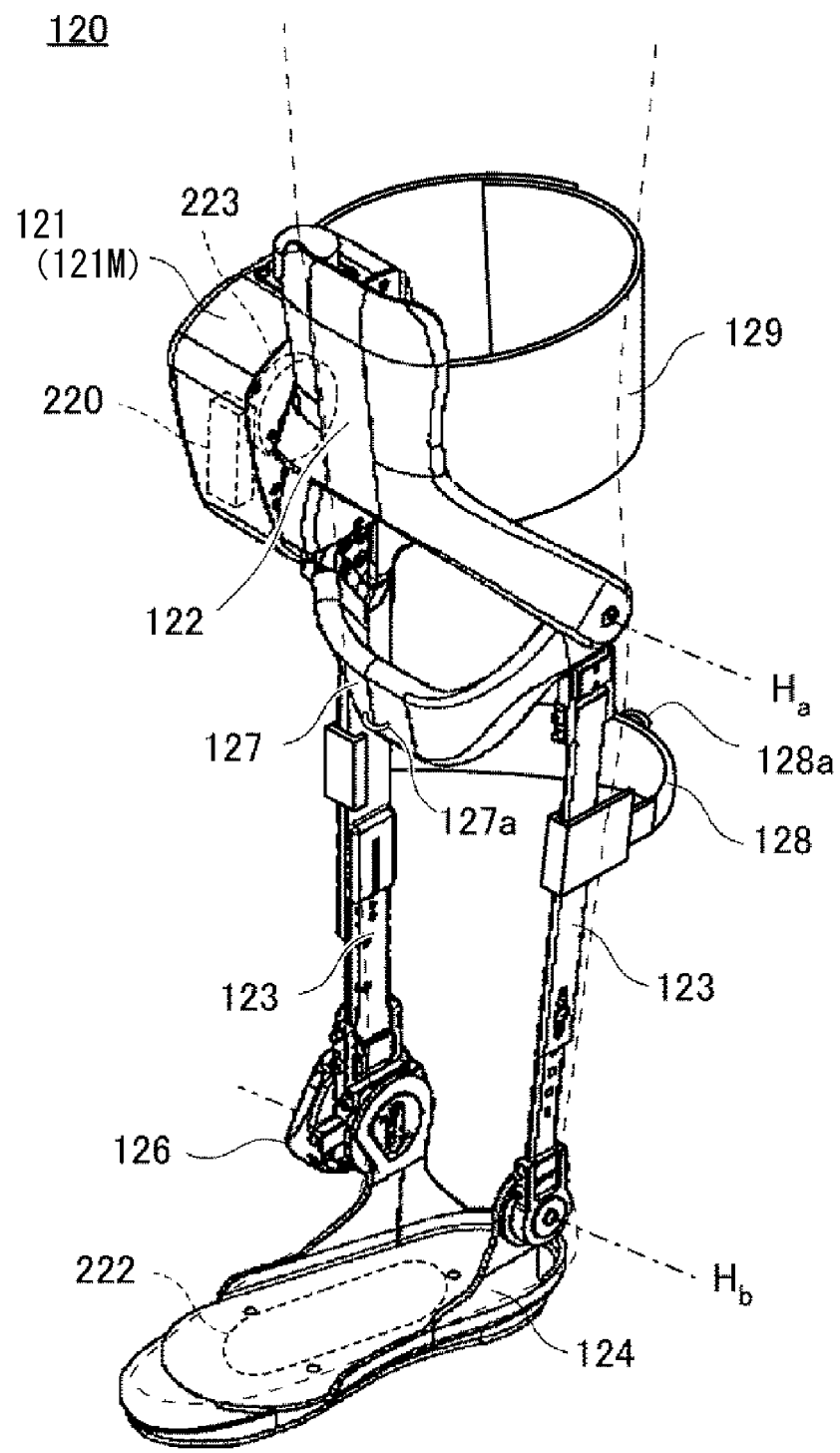
FIG. 2 is a schematic perspective view of the walking assistance apparatus.

Next, the walking assistance apparatus 120 will be described with reference to FIG. 2. FIG. 2 is a schematic perspective view showing an example of a configuration of the walking assistance apparatus 120. The walking assistance apparatus 120 mainly includes a control unit 121, a plurality of frames that support each part of a diseased leg, and a load sensor 222 for detecting a load (e.g., a pressure) applied to the sole.

The control unit 121 includes an assistance control unit 220 that controls the walking assistance apparatus 120, and also includes a motor(s) (not shown) that generates a driving force(s) for assisting extending movements and flexing movements of the knee joint. The frames, which support each part of the diseased leg, includes an upper-leg frame 122 and a lower-leg frame 123 rotatably connected to the upper-leg frame 122. Further, the frames also include a sole frame 124 rotatably connected to the lower-leg frame 123, a front connection frame 127 for connecting a front wire 134, and a rear connection frame 128 for connecting a rear wire 136.

The upper-leg frame 122 and the lower-leg frame 123 rotate relative to each other around a hinge axis $H_a$ shown in the drawing. A motor 121M of the control unit 121 rotates according to an instruction from the assistance control unit 220, and by doing so, force the upper-leg frame 122 and the lower-leg frame 123 to open relative to each other around the hinge axis $H_a$ or force them to close relative to each other. That is, the motor 121M is one of the drive units that are driven according to the trainee's motion in order to support the trainee's motion. The angle sensor 223 housed in the control unit 121 is, for example, a rotary encoder and detects an angle between the upper-leg frame 122 and the lower-leg frame 123 around the hinge axis $H_a$. The lower-leg frame 123 and the sole frame 124 rotate relative to each other around a hinge axis $H_b$ shown in the drawing. The angular range of their relative rotation is adjusted in advance by an adjustment mechanism 126.

The front connection frame 127 is disposed so as to extend in the left/right direction in front of the upper leg and is connected to the upper-leg frame 122 at both ends. Further, a connection hook 127a for connecting the front wire 134 is provided at or near the center of the front connection frame 127 in the left/right direction. The rear connection frame 128 is disposed so as to extend in the left/right direction behind the lower leg and is connected to the lower-leg frame 123 at both ends. Further, a connection hook 128a for connecting the rear wire 136 is provided at or near the center of the rear connection frame 128 in the left/right direction.

The upper-leg frame 122 includes an upper-leg belt 129. The upper-leg belt 129 is a belt integrally provided in the upper-leg frame and is wound around the upper leg of the diseased leg to fix the upper-leg frame 122 to the upper leg.

In this way, the whole walking assistance apparatus 120 is prevented from being displaced from the leg of the trainee 900.

The load sensor 222 is a load sensor embedded in the sole frame 124. The load sensor 222 may be configured to detect a magnitude and a distribution of a vertical load (e.g., a vertical pressure) received by the sole of the trainee 900. For example, the load sensor 222 may be configured to detect a COP (Center Of Pressure) of the sole. The load sensor 222 is, for example, a resistance change detection-type load detection sheet in which electrodes are arranged in a matrix pattern.

Figure 3:
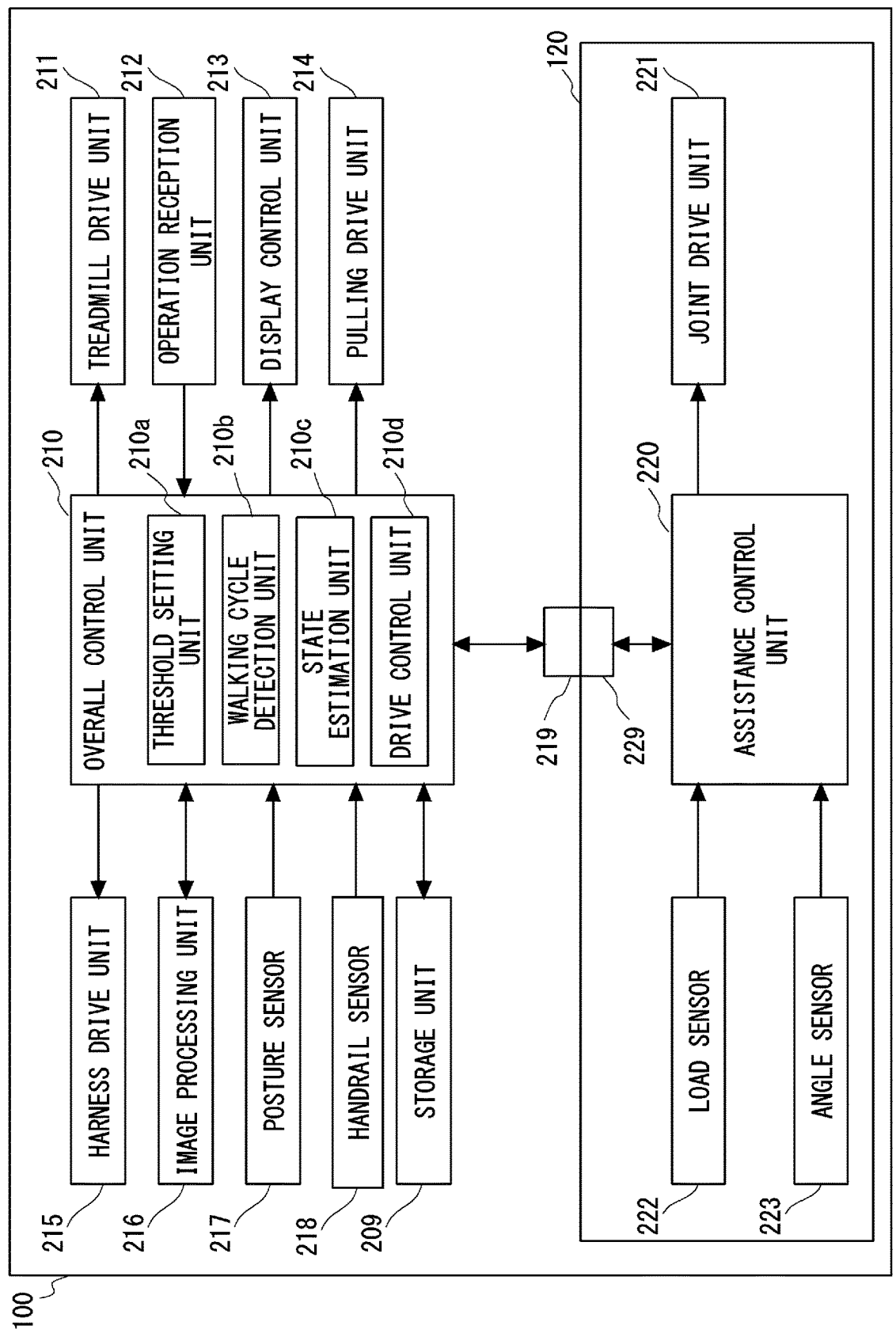
FIG. 3 is a block diagram showing a system configuration of the walking training apparatus according to the first embodiment.

Next, an example of a system configuration of the walking training apparatus 100 will be described with reference to FIG. 3. FIG. 3 is a block diagram showing an example of a system configuration of the walking training apparatus 100. As shown in FIG. 3, the walking training apparatus 100 may include an overall control unit 210, a treadmill drive unit 211, an operation reception unit 212, a display control unit 213, and a pulling drive unit 214. Further, the walking training apparatus 100 may include a harness drive unit 215, an image processing unit 216, a posture sensor 217, a handrail sensor 218, a communication connection IF (interface) 219, an input and output unit 231, and a walking assistance apparatus 120.

The overall control unit 210 is, for example, an MPU (Micro Processing Unit) and controls the overall operations of the apparatus by executing a control program loaded from a system memory. In this embodiment, the overall control unit 210 executes a state estimation program for estimating whether the training to be executed is in a normal state or an abnormal state. The overall control unit 210 evaluates whether the walking motion of the trainee 900 is abnormal or not by using, for example, data acquired from various sensors. The overall control unit 210 determines a training result of a series of walking trainings based on, for example, a cumulative number of the abnormal walking evaluated by the walking evaluation unit 210a. The overall control unit 210 can generate, as part of the rehabilitation data, a result of this determination or the cumulative number of the abnormal walking, based on which the determination result has been obtained. The overall control unit 210 includes a threshold setting unit 210a, a walking cycle detection unit 210b, a state estimation unit 210c, and a drive control unit 210d.

The threshold setting unit 210a acquires a sensor output, and sets a threshold for determining a normal state or an abnormal state of training from the acquired sensor output. A specific example of the setting of the threshold will be described later.

The walking cycle detection unit 210b detects a walking cycle of a trainee 900 under training. The walking cycle detection unit 210b determines, for example, whether the sole of the diseased leg is in contact with the treadmill 131, or whether it is a stance phase in which the sole is in contact with the treadmill 131 or in a swing phase in which the sole is not in contact with the treadmill 131, from data acquired from the load sensor 222 of the walking assistance apparatus 120. The walking cycle detection unit 210b detects a walking pattern of the trainee 900. The details of the walking cycle will be described later. The walking cycle detection unit 210b may recognize the trainee from an image of the trainee 900's body captured by the camera 140 in place of the data acquired from the load sensor 222, and detect a walking pattern from the recognized image of the trainee 900. The walking cycle detection unit 210b may detect a walking pattern from data generated by the load sensor 222 or the angle sensor 223 included in the walking assistance apparatus 120, instead of using the above-described means.

The state estimation unit 210c estimates whether the training is being performed in a normal state or an abnormal state based on the threshold set by the threshold setting unit. The drive control unit 210d controls the drive of the treadmill drive unit 211, the pulling drive unit 214, and the joint drive unit 221. For example, when the drive control unit 210d detects that the emergency stop button 232 has been pressed, it performs control for stopping the drive unit that is being driven.

The treadmill drive unit 211 includes a motor that rotates the belt 132 and its drive circuit. The overall control unit 210 controls the rotation of the belt 132 by sending a drive signal to the treadmill drive unit 211. The overall control unit 210 adjusts, for example, the rotational speed of the belt 132 according to a walking speed set by the training staff member 901.

The operation reception unit 212 receives an input operation from the training staff member 901 and transmits an operation signal to the overall control unit 210. The training staff member 901 operates operation buttons provided in the apparatus, a touch panel disposed over the management monitor 139, an accessory remote controller, etc., which constitute the operation reception unit 212. By the above-described operation, the training staff member 901 can turn on/off the power, provide an instruction to start training, enter a numerical value for the setting, and select a menu item. The operation reception unit 212 also receives an operation of the emergency stop button 232. By this operation, the training staff member 901 can stop the drive unit of the walking training apparatus 100 in an emergency during training. Note that the operation reception unit 212 can also receive an input operation from the trainee 900.

The display control unit 213 receives a display signal from the overall control unit 210, generates a display image, and displays the generated display image on the training monitor 138 or the management monitor 139. The display control unit 213 generates an image showing progress of the training and a real-time video image shot by the camera 140.

The pulling drive unit 214 includes a motor for pulling the front wire 134 and its drive circuit, which constitute the front pulling unit 135, and a motor for pulling the rear wire 136 and its drive circuit, which constitute the rear pulling unit 137. The overall control unit 210 controls winding of the front wire 134 and winding of the rear wire 136 by sending a drive signal(s) to the pulling drive unit 214. Further, the pulling force of each wire is controlled by controlling the driving torque of the respective motor in addition to controlling the winding operation. The overall control unit 210 identifies (i.e., determines), for example, a timing at which the diseased leg changes from a stance state to a swing state from the result of the detection by the load sensor 222, and assists the swinging action of the diseased leg by increasing or decreasing the pulling force of each wire in synchronization with the identified timing.

The harness drive unit 215 includes a motor for pulling the harness wire 111 and its drive circuit, which constitute the harness pulling unit 112. The overall control unit 210 controls winding of the harness wire 111 and the pulling force of the harness wire 111 by sending a drive signal(s) to the harness drive unit 215. For example, when the overall control unit 210 predicts that the trainee 900 will fall down, it prevents the trainee from falling down by winding the harness wire 111 by a certain length.

The image processing unit 216 is connected to the camera 140, so that it can receive an image signal from the camera 140. The image processing unit 216 receives an image signal from the camera 140 according to an instruction from the overall control unit 210, and generates image data by performing image processing on the received image signal. Further, the image processing unit 216 can also perform a specific image analysis by performing image processing on the image signal received from the camera 140 according to an instruction from the overall control unit 210. For example, the image processing unit 216 detects the position of the foot of the diseased leg at which the foot is in contact with the treadmill 131 (i.e., a stance position) by the image analysis. Specifically, for example, the image processing unit 216 extracts an image area near the tip of the sole frame 124, and calculates the stance position by analyzing an identification marker drawn on a part of the belt 132 where the tip of the sole frame 124 is located.

The posture sensor 217 detects an inclination angle of the abdomen of the trainee 900 with respect to the direction of gravity as described above, and transmits a detection signal to the overall control unit 210. The overall control unit 210 calculates the posture of the trainee 900, in particular, an inclination angle of his/her trunk by using the detection signal from the posture sensor 217. Note that the overall control unit 210 and the posture sensor 217 may be connected to each other through a cable or through short-range wireless communication.

The handrail sensor 218 detects a load (e.g., a pressure) applied to the handrail 130a. That is, the amount of the load corresponding to the part of the trainee's own weight that the trainee 900 cannot support by both legs is applied to the handrails 130a. The handrail sensor 218 detects this load and transmits a detection signal to the overall control unit 210.

The storage unit 209 is a storage device including a volatile memory such as a DRAM (Dynamic Random Access Memory) and a non-volatile memory such as a flash memory, an SSD (Solid State Drive), or an HDD (Hard Disc Drive). The storage unit 209 stores a threshold and the like set by the threshold setting unit 210a.

The communication connection IF 219 is an interface connected to the overall control unit 210, and is an interface for providing an instruction to the walking assistance apparatus 120 attached to the diseased leg of the trainee 900 and receiving sensor information therefrom.

The walking assistance apparatus 120 may include a communication connection IF 229 that is connected to the communication connection IF 219 through a cable or wirelessly. The communication connection IF 229 is connected to the assistance control unit 220 of the walking assistance apparatus 120. The communication connection IFs 219 and 229 are communication interfaces in conformity with communication standards, such as those of a wired LAN or a wireless LAN.

Further, the walking assistance apparatus 120 may include an assistance control unit 220, a joint drive unit 221, a load sensor 222, and an angle sensor 223. The assistance control unit 220 is, for example, an MPU and controls the walking assistance apparatus 120 by executing a control program supplied from the overall control unit 210. Further, the assistance control unit 210 notifies the overall control unit 220 of the state of the walking assistance apparatus 120 through the communication connection IFs 229 and 219. Further, the assistance control unit 220 performs control of walking assistance apparatus 120, such as the start/stop thereof, in response to a command from the overall control unit 210.

The joint drive unit 221 includes the motor 121M of the control unit 121 and its drive circuit. The assistance control unit 220 sends a drive signal to the joint drive unit 221 to force the upper-leg frame 122 and the lower-leg frame 123 to open relative to each other around the hinge axis $H_a$ or force them to close relative to each other. Through the above-described operations, the assistance control unit 220 assists an extending motion and a flexing motion of the knee and prevents the knee from buckling. That is, the joint drive unit 221 is one of the drive units that are driven according to the trainee's motion in order to support the trainee's motion.

The joint drive unit 221 can switch a driving force of the motor 121M of the control unit 121 to a preset level. The switching of the driving force of the motor 121M in the control unit 121 is set as an assistance level. That is, the assistance level in this embodiment indicates the strength of an assistance operation performed for the trainee 900 performing walking training.

The load sensor 222 detects the magnitude and the distribution of the vertical load (e.g., the vertical pressure) applied to the sole of the trainee 900 and transmits a detection signal to the assistance control unit 220 as described above. The assistance control unit 220 can receive and analyze the detection signal, and thereby determines the swing/stance state.

The angle sensor 223 detects the angle between the upper-leg frame 122 and the lower-leg frame 123 around the hinge axis $H_a$ and transmits a detection signal to the assistance control unit 220 as described above. The assistance control unit 220 receives this detection signal and calculates the open angle (knee extension angle) of the knee joint.

(Walking Cycle)

Figure 4:
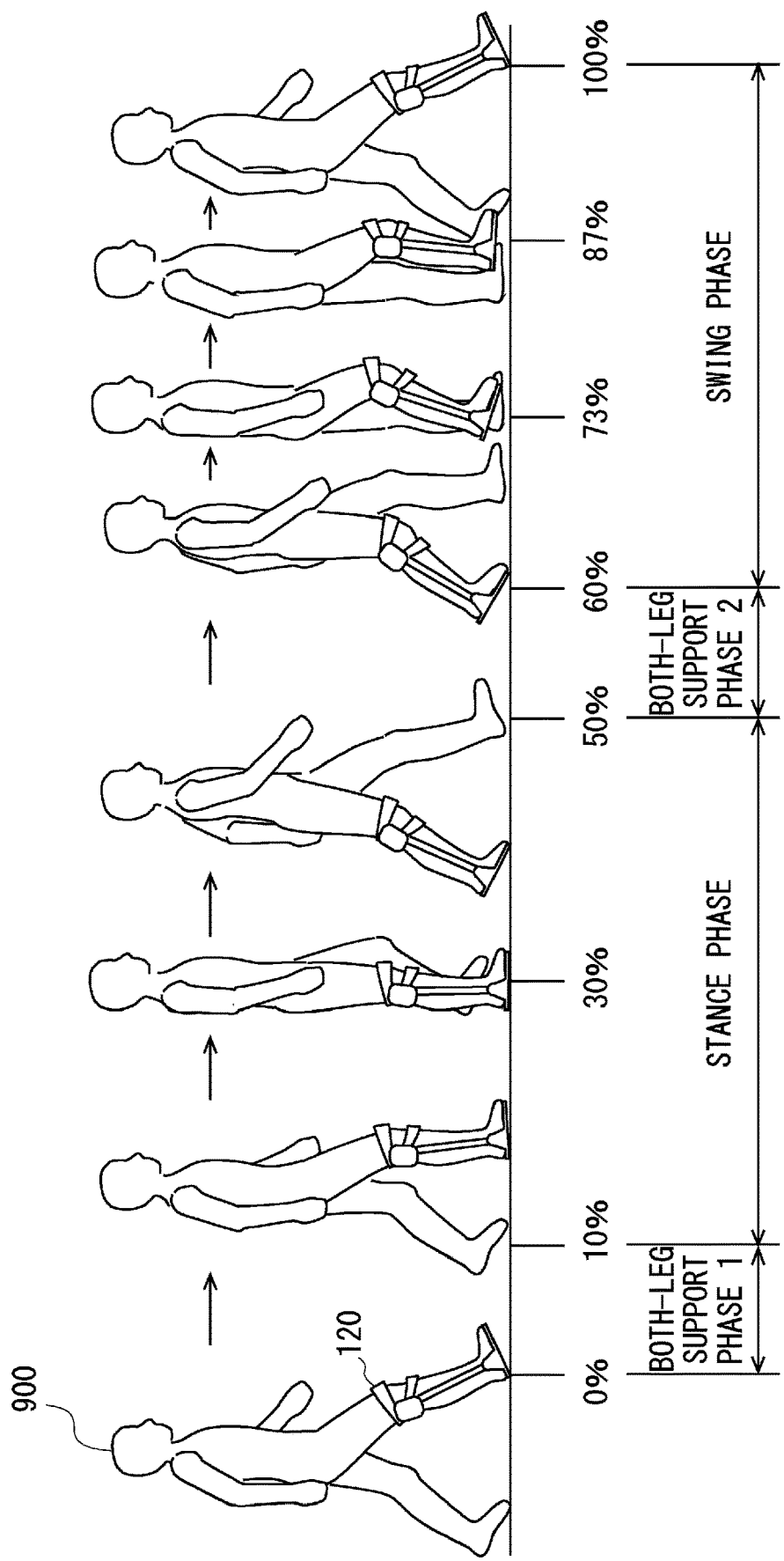
FIG. 4 shows an example of a walking cycle of a trainee.

The walking cycle of the trainee 900 will be described with reference to FIG. 4. FIG. 4 shows an example of the walking cycle of the trainee. FIG. 4 shows a walking trajectory for one cycle focusing on the right leg, which is the diseased leg of the trainee 900 walking from left to right. The walking trajectory is shown as 0% at a position where the right leg comes into contact with the floor surface, and 100% at a position where the right leg has walked for one cycle.

A walking cycle of one cycle is classified into 0 to 10% both-leg support phase 1, 10 to 50% stance phase, 50 to 60% both-leg support phase 2, and 60 to 100% swing phase. The both-leg support phase 1 is an initial stance phase, and the left leg, which is the leg opposite to the right leg, is also in contact with the floor surface. In the stance phase, the right leg (diseased leg), which is the leg of interest, comes into contact with the floor surface, and the left leg, which is the leg opposite to the right leg, is away from the floor surface. The both-leg support phase 2 is a terminal stance phase, and the left leg, which is the leg opposite to the right leg, also comes into contact with the floor surface. In the swing phase, the right leg, which is the leg of interest, is away from the floor surface.

The trainee 900 suffering from paralysis in the right leg may have difficulty supporting his/her weight during the stance phase of the walking cycle shown in the drawing. In such a case, the trainee 900's knee may greatly bend, resulting in "knee buckling". The knee buckling refers to a state in which, as the knee extension function deteriorates, the knee bends, and the trainee 900 cannot maintain the extending of his/her knee, and thus he/she unconsciously bends his/her knee while walking. Further, although the trainee 900 needs to extend his/her knee at the position around 30% of the walking cycle, he/she may not be able to extend his/her knee after bending his/her knee. Thus, the motor 121M of the control unit 121 is driven so as to prevent the knee from excessively bending or assist the knee to extend at a predetermined timing during the stance phase.

Figure 5:
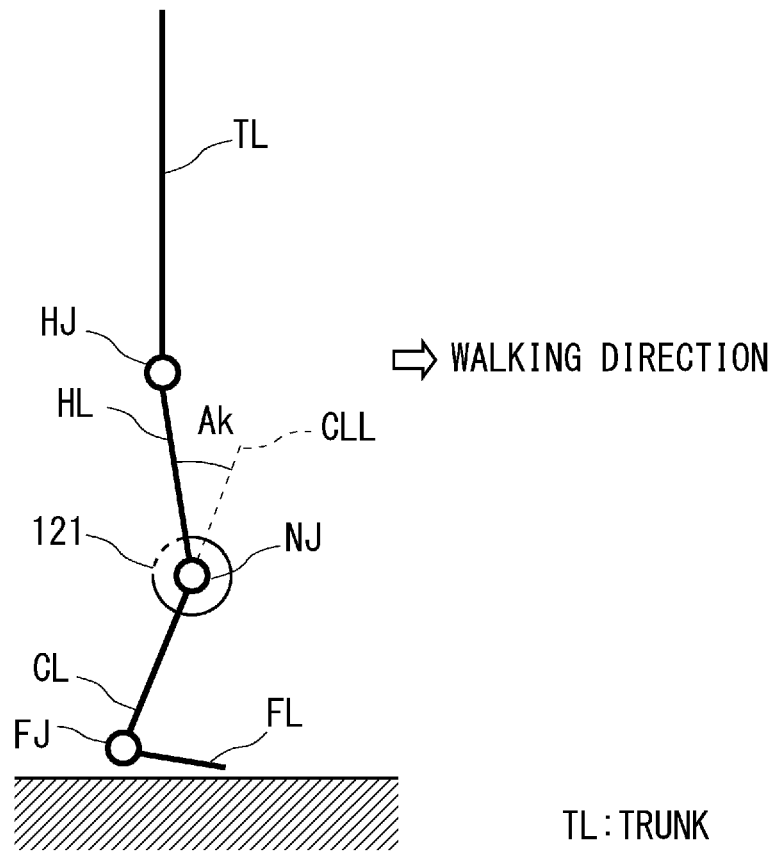
FIG. 5 shows an example of a knee extension angle of a diseased leg.

Next, an angle of the knee joint will be described with reference to FIG. 5. FIG. 5 shows an example of a knee extension angle of the diseased leg. The knee extension angle of the diseased leg is an example of a walking posture of the trainee 900. FIG. 5 is a schematic diagram when the paralyzed body part, which is the lower body of the diseased leg, is observed from the side with respect to the walking direction. FIG. 5 shows a trunk TL, a hip joint HJ, an upper leg HL, a knee joint NJ, a lower leg CL, an ankle joint FJ, and a foot FL in order from the top. A lower leg extension line CLL is indicated by a dotted line as an extension line extending the lower leg CL upward. An angle between the upper leg HL and the lower leg extension line CLL is shown as a knee extension angle Ak. In the schematic diagram of FIG. 5, the diseased leg of the trainee 900 is in the stance phase and is in contact with the floor surface.

The knee extension angle Ak of a healthy subject in the stance phase shown in the drawing is 10 to 15 degrees. Thus, the maximum knee extension angle Ak in the stance phase may be about 10 to 15 degrees even for the trainee 900 when he/she walks. However, when the trainee 900 cannot support his/her weight, the knee extension angle Ak may become much greater than 15. Thus, the motor 121M of the control unit 121 attached to the knee joint NJ is driven in a direction to return the knee extension angle Ak to within a predetermined range when the knee extension angle A exceeds a preset value.

Figure 6:
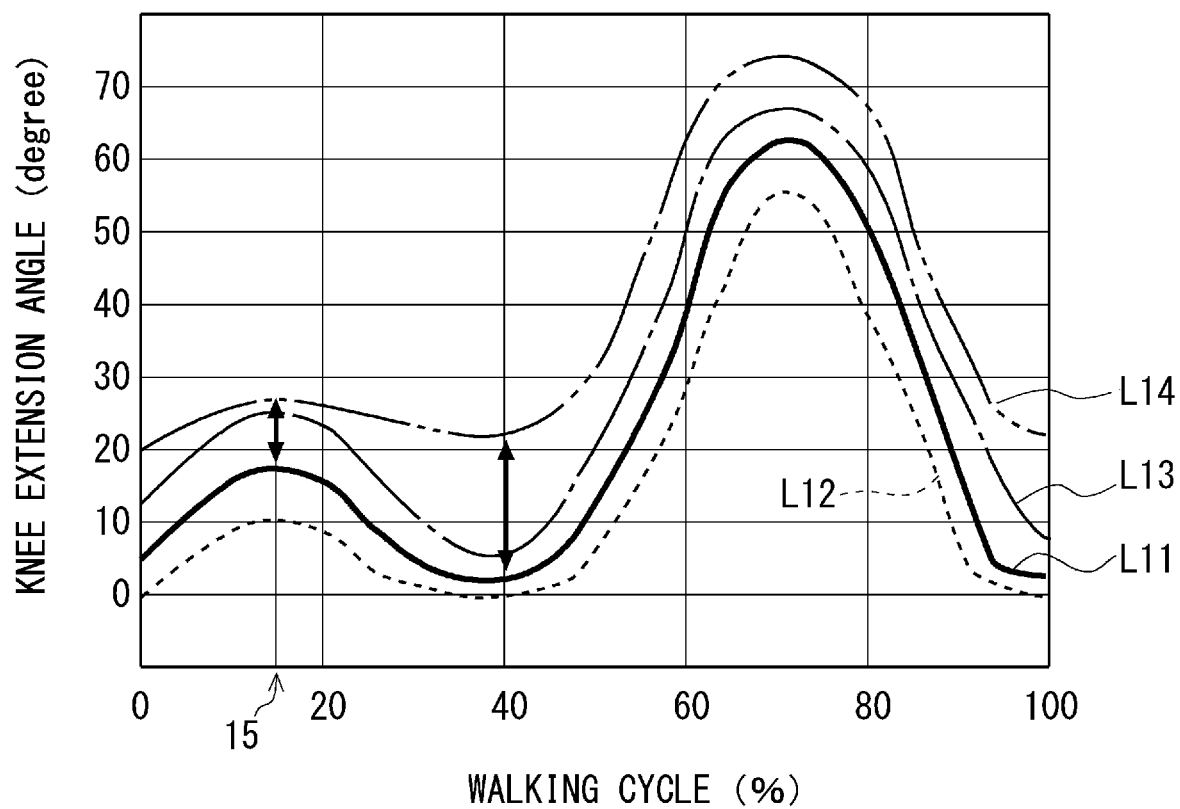
FIG. 6 shows a relationship between a walking cycle and a knee extension angle.

Next, an example of a principle for detecting a walking cycle using the knee extension angle Ak and setting a threshold for estimating a training state will be described with reference to FIG. 6. FIG. 6 shows a relationship between the walking cycle and the knee extension angle. In the graph of FIG. 6, the horizontal axis represents the walking cycle, and the vertical axis represents the knee extension angle. A curve L11 plotted as the solid line in the graph is a walking trajectory showing a change in the knee extension angle Ak indicating the walking posture of the trainee 900 in walking training that has been performed normally.

As shown in the drawing, the knee joint is extended and flexed twice during a walking cycle. The trainee 900's leg makes an initial contact with the treadmill with a bending position of about 5 degrees at a walking cycle of 0%, and then the leg is flexed to about 15 degrees before the leg is extended. The trainee 900's leg is then extended almost completely till 40% of the walking cycle, and then begins to be flexed again. Maximum flexion occurs at the beginning of a mid-swing phase (around 70% of walking cycle), when the knee extension angle Ak is about 60 degrees. From the mid-swing phase onward, the trainee 900's leg is extended to an almost complete extension position (knee extension angle Ak is around 0 degrees) for the next initial contact with the treadmill.

While the training is performed normally, the trainee 900's leg repeats the pattern shown as the curve L11. The angle sensor 223 recognizes the walking cycle by detecting the knee extension angle Ak during training at predetermined intervals. The data of the walking cycle shown as the curve L11 may be generated by calculating a statistical value such as an average value from the data of a plurality of walking cycles.

A curve L12 indicated by the dotted line in the drawing is an example of a threshold on the lower limit side set by the threshold setting unit 210a. L12 is set, for example, by calculating a standard deviation from the data of walking performed a plurality of times by the trainee 900 and setting the calculated standard deviation. That is, this threshold is set on the assumption that the walking pattern of the trainee 900 under normal training does not fall below the curve L12. Thus, when the knee extension angle Ak falls below the curve L12 during the training, the state estimation unit 210c estimates that the training state is the abnormal state.

Likewise, a curve L13 indicated by the dashed line in the drawing is an example of a first threshold on the upper limit side set by the threshold setting unit 210a. L13 is set from a standard deviation acquired by calculating a standard deviation from the data of walking performed a plurality of times by the trainee 900 in a manner similar to the threshold on the lower limit side. Thus, when the knee extension angle Ak falls below the curve L13 during the training, the state estimation unit 210c estimates that the training state is the abnormal state.

A curve L14 indicated by the two-dot chain line in the drawing is an example of a second threshold on the upper limit side set by the threshold setting unit 210a. The second threshold indicated by the curve L14 is set at an angle larger than the first threshold indicated by the curve L13. Thus, the threshold setting unit 210a can change the threshold settings on the upper limit side and the lower limit side.

The threshold setting unit 210a may appropriately change the setting mode of the threshold according to the timing of the walking cycle. For example, a difference between the second threshold and the curve L11 in the walking cycle of 15% is set smaller than a difference between the second threshold and the curve L11 in the walking cycle of 40%. The threshold setting unit 210a performs such setting by previously having a weighting value such as a coefficient to be multiplied with the threshold in accordance with the timing of the walking cycle. The threshold setting unit 210a may change the threshold by a user operation. Thus, by changing the setting mode of the threshold according to the timing of the walking cycle, the walking training apparatus 100 can effectively estimate the state of the training.

Figure 7:
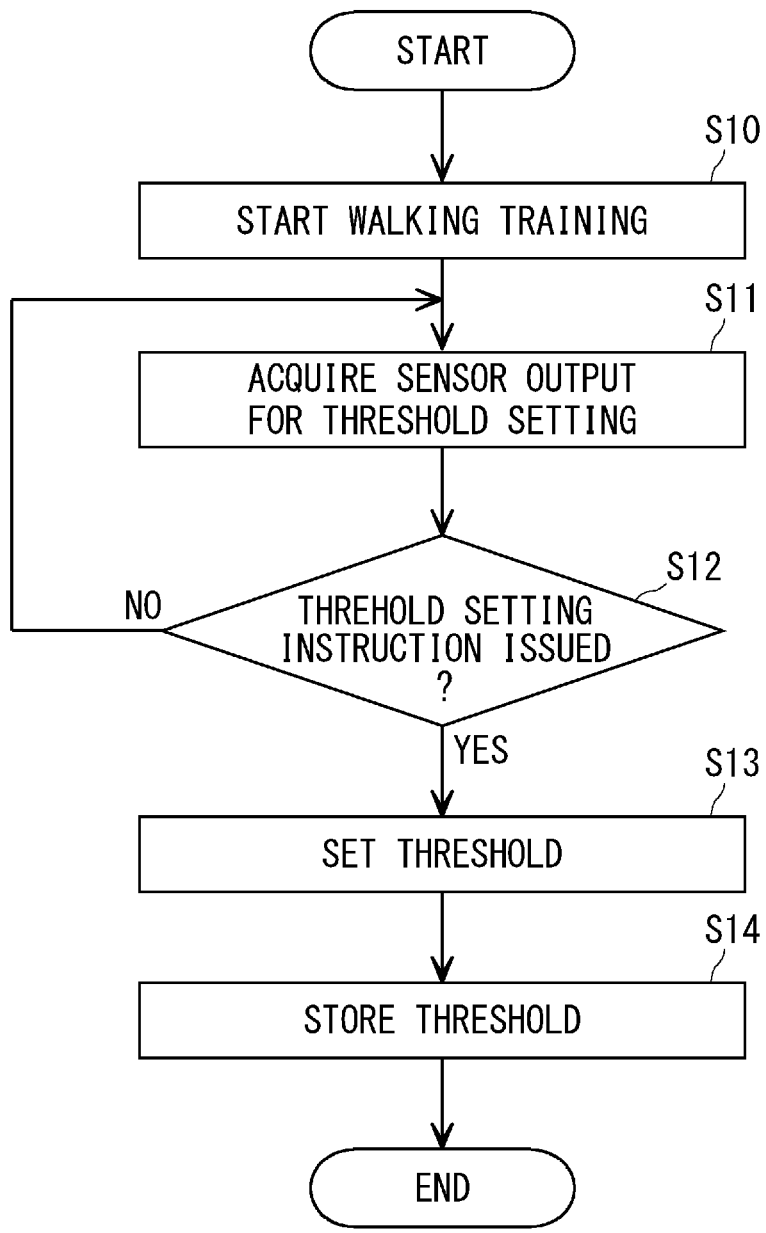
FIG. 7 is a flowchart showing processing in which the walking training apparatus sets a threshold.

Next, processing in which the walking training apparatus 100 sets a threshold will be described with reference to FIG. 7. FIG. 7 is a flowchart showing processing in which the walking training apparatus 100 sets a threshold. The flowchart of the drawing shows the processing of the overall control unit 210 when the threshold is set from the sensor output in the normal state.

First, the overall control unit 210 performs processing for starting the walking training (step S10). When the trainee 900 starts walking, the overall control unit 210 acquires a sensor output for setting the threshold (step S11). The sensor output for setting the threshold may be data of training in a normal state performed by the trainee 900 and may be data including a plurality of data pieces such as, for example, for 100 steps.

Next, the overall control unit 210 determines whether there has been an instruction for setting a threshold using the acquired sensor output (step S12). The instruction for setting a threshold is transmitted to the overall control unit 210 by, for example, the training staff member 901 performing a predetermined operation.

When the walking training for setting a thresholds includes an abnormal state, the training staff member 901 does not instruct the setting of the threshold. In this case, the overall control unit 210 does not determine that the threshold setting instruction has been issued (step S12: NO), and returns to step S11 to acquire the sensor output again.

On the other hand, when the walking training for setting a threshold is normally performed, the training staff member 901 instructs the setting of the threshold. In this case, the overall control unit 210 determines that a threshold setting instruction has been issued (step S12: YES), and sets a threshold (step S13). When the threshold is set, the overall control unit 210 controls the storage unit 209 to store the threshold so that the set threshold can be used in training to be performed thereafter (step S14).

Figure 8:
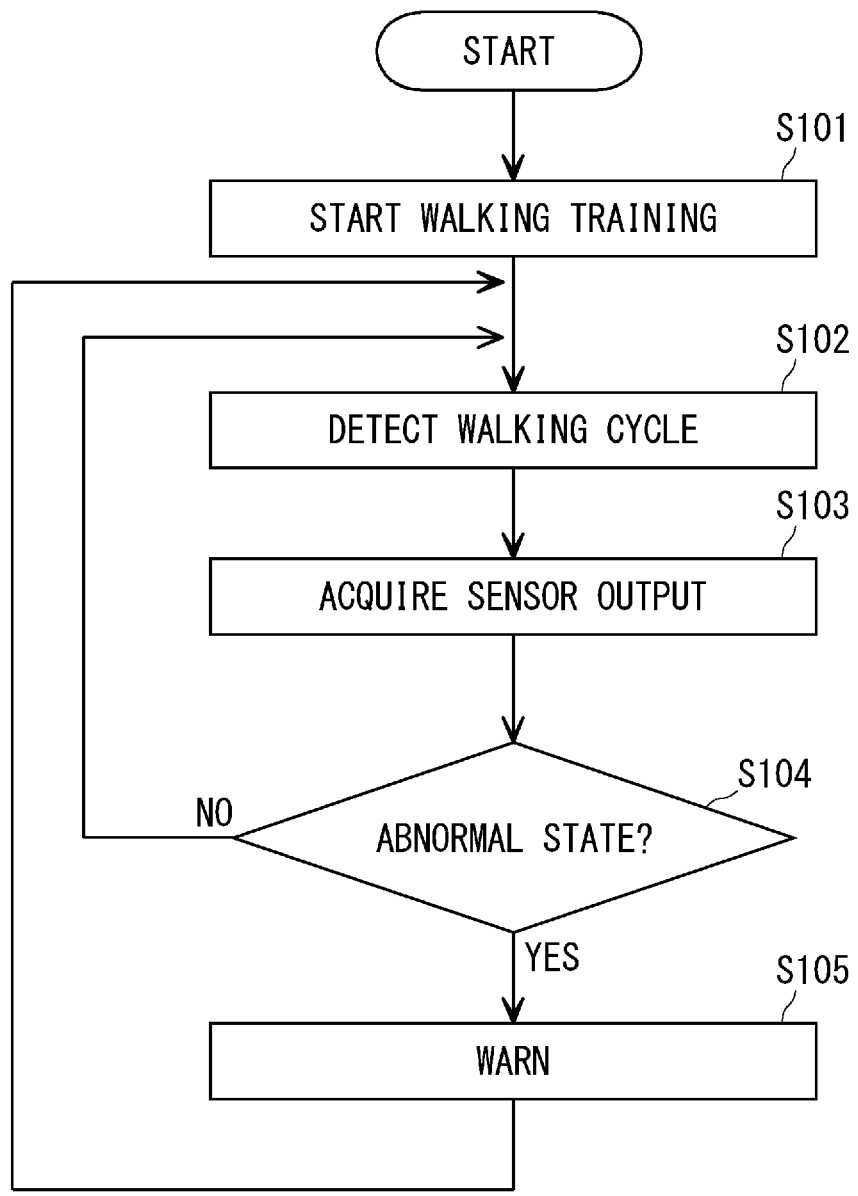
FIG. 8 is a flowchart showing processing of the walking training apparatus according to the first embodiment.

Next, the processing performed by the walking training apparatus 100 during training will be described with reference to FIG. 8. FIG. 8 is a flowchart showing the processing of the walking training apparatus according to the first embodiment. The flowchart shown in FIG. 8 is processing performed by the overall control unit 210 when the trainee 900 performs walking training.

First, the overall control unit 210 performs processing for starting the walking training (step S101). When the trainee 900 starts walking, the overall control unit 210 detects a walking cycle (step S102). Specifically, the walking cycle detection unit 210b detects the walking cycle from the output of the angle sensor 223, for example, as shown in FIG. 6.

Next, the overall control unit 210 acquires a sensor output from the walking training apparatus 100 under training (step S103). For example, the overall control unit 210 acquires an output from the angle sensor 223 corresponding to the detected walking cycle.

Next, the state estimation unit 210c of the overall control unit 210 estimates whether the training being performed is in an abnormal state (step S104). The training being performed is estimated to be in the abnormal state by detecting that the acquired sensor output is not below the threshold, for example, as shown in FIG. 6.

When it is not estimated that the training being performed is in the abnormal state (Step S104: NO), the overall control unit 210 returns to step S102 and detects the walking cycle again. On the other hand, when it is estimated that the training being performed is in the abnormal state (step S104: YES), the overall control unit 210 issues a warning (step S105). The warning is issued, for example, by displaying a message such as "Abnormal state" or "Stop training" on the training monitor 138. The warning may be issued by a voice, light or the like in addition to the display of the message or in place of the display of the message. The overall control unit 210 instructs the display control unit 213 to display such a warning display on the training monitor 138 for a predetermined period of time, for example, 3 seconds or 5 seconds. Next, after the processing for the warning display, the overall control unit 210 returns to step S102 to detect a walking cycle.

In this manner, the walking training apparatus 100 issues a warning when the abnormal state is estimated. By suitably setting a threshold for warning, the training staff member 901 can perform an operation to ensure the safety of the trainee 900, such as pressing the emergency stop button 232 before the trainee 900 falls down or the like. Thus, according to this embodiment, it is possible to provide a state estimation program and the like for effectively preventing lowering of a trainee's safety.

The state estimation unit 210c may set a threshold for a preset period or timing in the walking cycle to determine the state. For example, the state estimation unit 210c may determine the state at a preset timing (e.g., the position of 15% of the walking cycle) in the walking cycle. Further, the state estimation unit 210c may discretize the walking cycle and determine the state at the discretized timing.

First Modified Example of First Embodiment

Next, a first modified example of the first embodiment will be described. The threshold setting unit 210a according to this modified example acquires profile data of the trainee in addition to the sensor output, and sets a threshold using the sensor output and the profile data.

Figure 9:
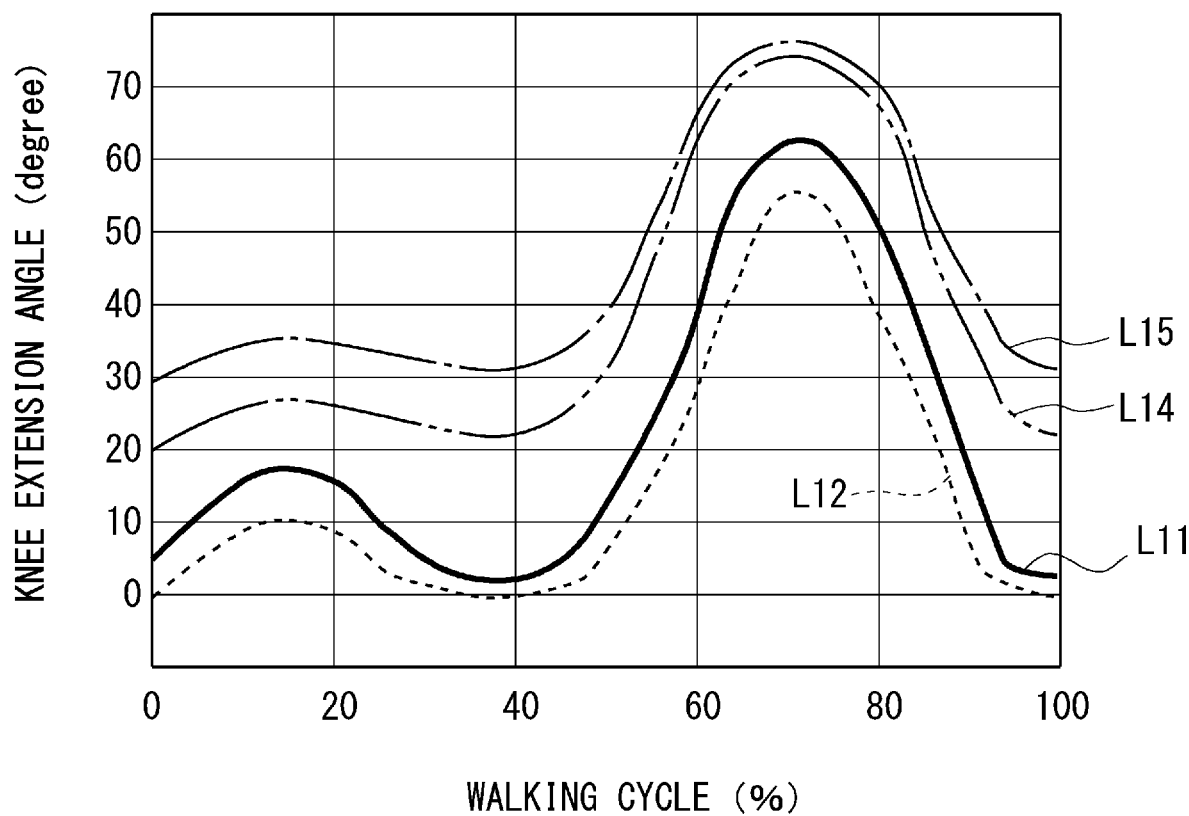
FIG. 9 shows a relationship between the walking cycle and the knee extension angle.

FIG. 9 shows a relationship between the walking cycle and the knee extension angle according to the first modified example of the first embodiment. In FIG. 9, a curve L15 is plotted above the curve L14 shown in FIG. 6. The threshold in the stance phase (1% to 50%) is set larger for the curve L15 than that for the curve L14. Different thresholds are set for the curves L14 and L15 in this way, because there is a difference in the profile data of the trainee for which the threshold of the curve L14 is set and the profile data of the trainee for which the threshold of the curve L15 is set.

(Profile Data)

The profile data will be described here. The profile data acquired by the threshold setting unit 210a indicates information about the trainee and is, for example, a cognitive level based on a functional independence measure. As a method for evaluating the trainee's cognitive level, for example, FIM (Functional Independence Measure) is known. The FIM is one of the evaluation methods for evaluating ADL (Activities of Daily Life). In the FIM, a patient is evaluated (i.e., classified) into seven stages, i.e., one point to seven points according to the level of assistance.

The profile data may be the trainee's assessment score based on a stroke impairment assessment set. There is, for example, SIAS (Stroke Impairment Assessment Set) as an assessment method for quantifying an index for dysfunction caused by a stroke the trainee is suffering from. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

The profile data may be data indicating attributes of the trainee. The data indicating attributes of the trainee include, for example, the trainee's age, sex, physique (height, weight, etc.), and a score indicating the trainee's physical condition.

The profile data acquired by the threshold setting unit 210a is, for example, a coefficient generated corresponding to a score included in at least one of the above-described information. In this case, the threshold setting unit 210a sets a threshold by multiplying a value calculated from the acquired sensor output by a coefficient generated from the profile data.

For example, an FIM score related to walking of the trainee for whom the threshold of the curve L14 shown in FIG. 9 is set differs from that of the trainee for whom the threshold of the curve L15 is set. In such a case, the threshold setting unit 210a sets different thresholds for these trainees even when the sensor outputs are the same.

Figure 10:
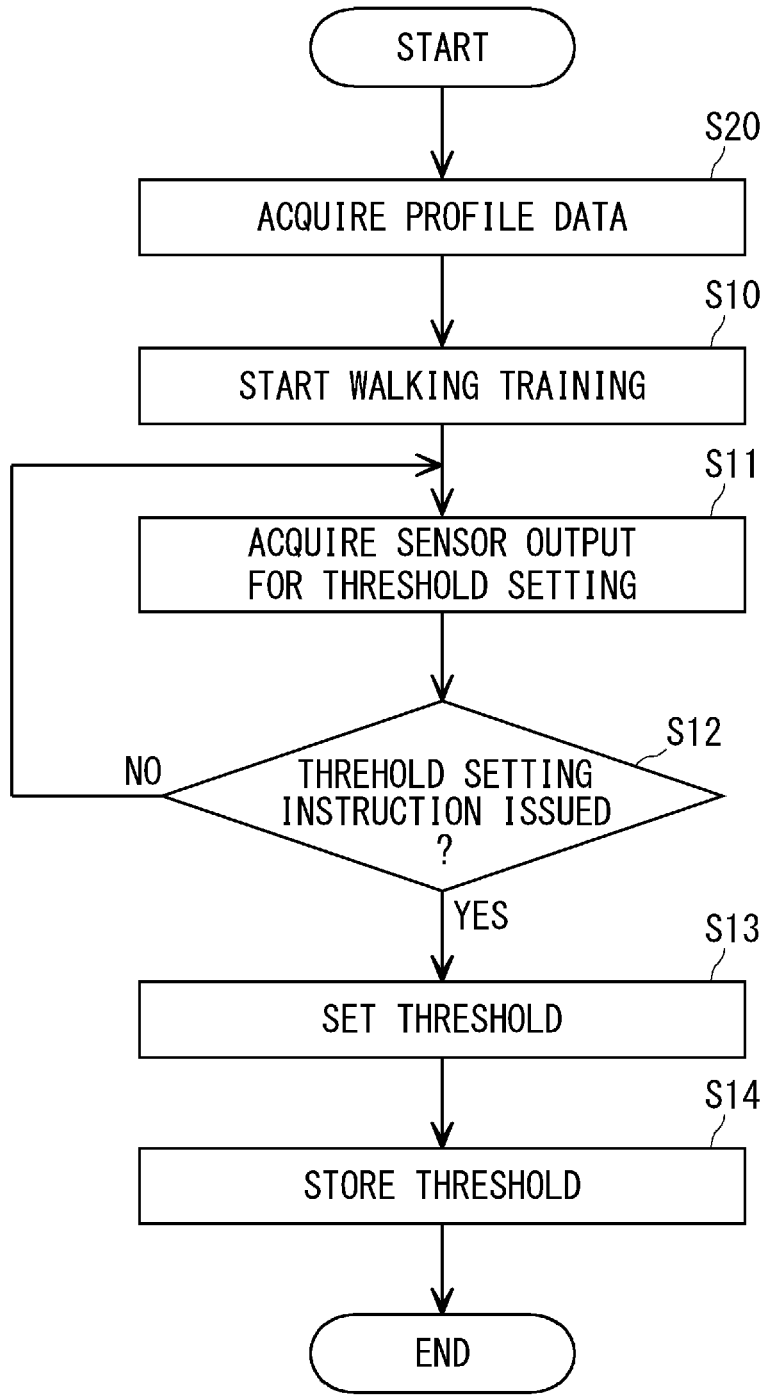
FIG. 10 is a flowchart showing a second example of processing for setting a threshold.

Next, processing according to the first modified example of the first embodiment will be described with reference to FIG. 10. FIG. 10 is a flowchart showing another example of processing performed by the overall control unit 210 according to the first modified example of the first embodiment. The flowchart shown in FIG. 10 differs from the flowchart shown in FIG. 7 in that step S20 is added before step S10 in the flowchart of FIG. 10. Hereinafter, the processing of the overall control unit 210 will be described, while the description of processing the same as that of the processing shown in FIG. 7 is omitted.

When the processing according to the first modified example of the first embodiment is performed, the threshold setting unit 210a first acquires profile data (step S20). The profile data is input to the walking training apparatus 100 by an operation performed by the training staff member 901 or the like.

Next, in a manner similar to the processing shown in FIG. 7, the overall control unit 210 performs processing for starting walking training (step S10), and further acquires a sensor output for setting a threshold (step S11). When walking training for setting a threshold is normally performed, the training staff member 901 instructs setting of the threshold. In this case, the overall control unit 210 determines that a threshold setting instruction has been given (Step S12: YES), and sets the threshold (step S13).

In order to set the threshold, the overall control unit 210 performs calculation using the acquired sensor output and profile data. When the threshold is set, the overall control unit 210 controls the storage unit 209 to store the threshold so that the set threshold can be used in training to be performed thereafter (step S14).

By using the profile data as described above, the walking training apparatus 100 can suitably set a threshold in accordance with the profile data of the trainee 900. When the profile data of the trainee 900 is acquired and the threshold is set, training is started after the profile data of the trainee is input in order to execute the state estimation program. By performing such processing, it is possible to set a suitable threshold for each trainee and perform training.

Second Modified Example of First Embodiment

Figure 11:
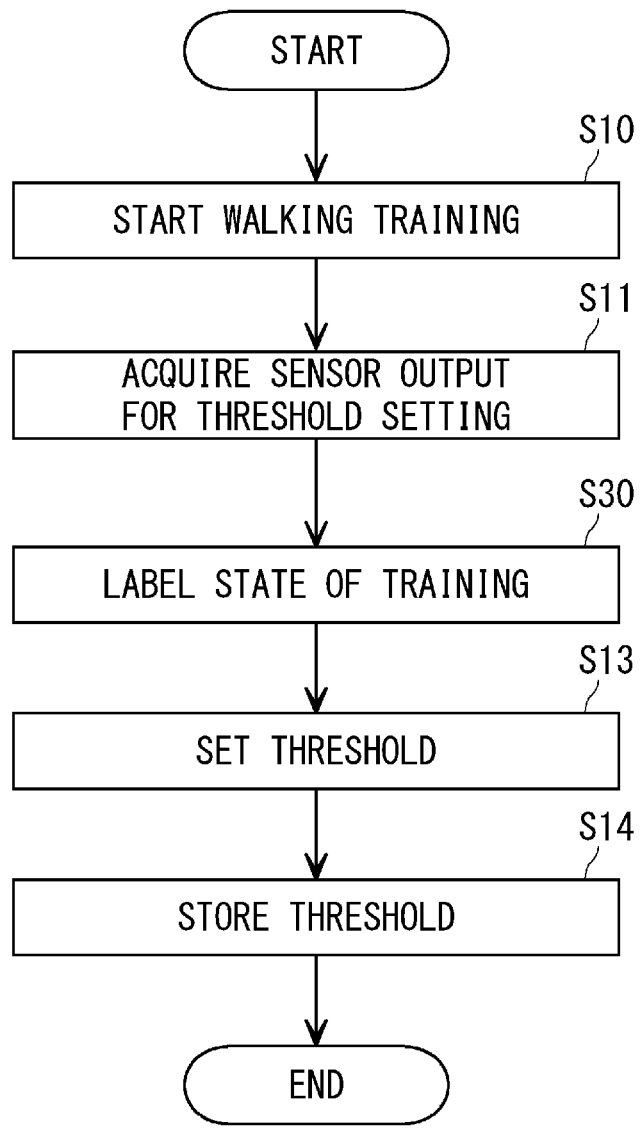
FIG. 11 is a flowchart showing a third example of processing for setting a threshold.

Next, a second modified example of first embodiment will be described with reference to FIG. 11. FIG. 11 is a flowchart showing processing performed by the threshold setting unit 210a according to the second modified example of the first embodiment. The flowchart of this modified example differs from that shown in FIG. 7 in that step S30 is included in place of step S12 in the flowchart of FIG. 11. That is, in this modified example, the walking training apparatus 100 acquires a sensor output for setting a threshold (step S11), and labels the training state related to the acquired sensor output (step S30).

More specifically, the walking training apparatus 100 labels the walking training performed to acquire the sensor output for setting a threshold to indicate whether the walking training is in a normal state or an abnormal state. In the labeling for indicating whether the training is in a normal state or an abnormal state, for example, the training staff member 901 performs an operation of appropriately determining whether the training is in a normal state or an abnormal state and labels the training for each training performed.

The walking training apparatus 100 according to this modified example calculates a boundary between the normal state and the abnormal state by acquiring the sensor outputs for the normal state and the abnormal state, respectively. As a method for calculating the boundary between the normal state and the abnormal state, the walking training apparatus 100 can use, for example, SVM (support vector machine).

Figure 12:
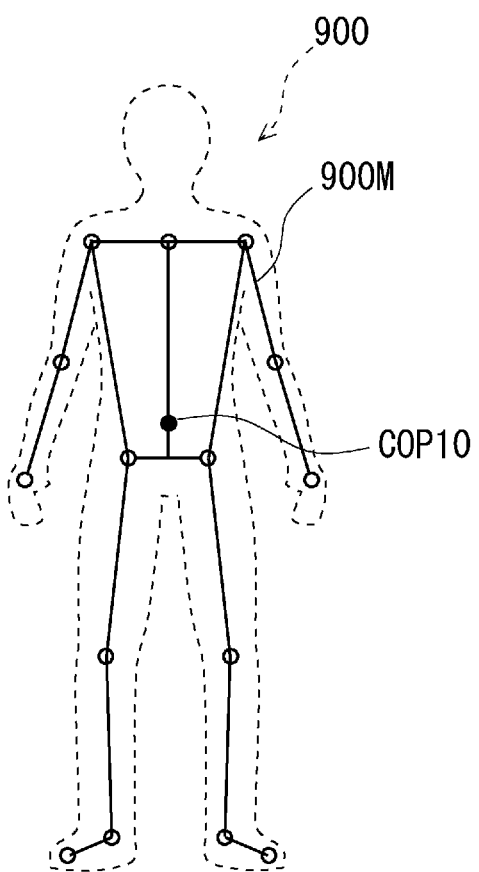
FIG. 12 shows a first example of a threshold set from image data.

Although a configuration example of the first embodiment has been described above, the first embodiment is not limited to the above-described configuration. Other examples of sensor outputs will be described below. FIG. 12 shows a first example of a threshold set from image data. A skeleton model 900M shown in FIG. 12 is a skeleton model of the trainee 900 generated by capturing an image of the trainee 900. The walking training apparatus 100 is generated by processing the image of the trainee 900 captured by the camera 140. The overall control unit 210 generates the skeleton model 900M, and estimates a center of gravity COP 10 of the trainee 900 from the generated skeleton model 900M. Note that techniques for capturing images of a person, generating such a skeleton model from image data of the captured image, and estimating the center of gravity are known to those skilled in the art. Thus, the detailed description of such techniques is omitted here.

Under such a situation, the overall control unit 210 detects a walking cycle of the trainee 900 and estimates the state of the training by, for example, performing a process of tracking the center of gravity COP 10 at predetermined intervals.

Figure 13:
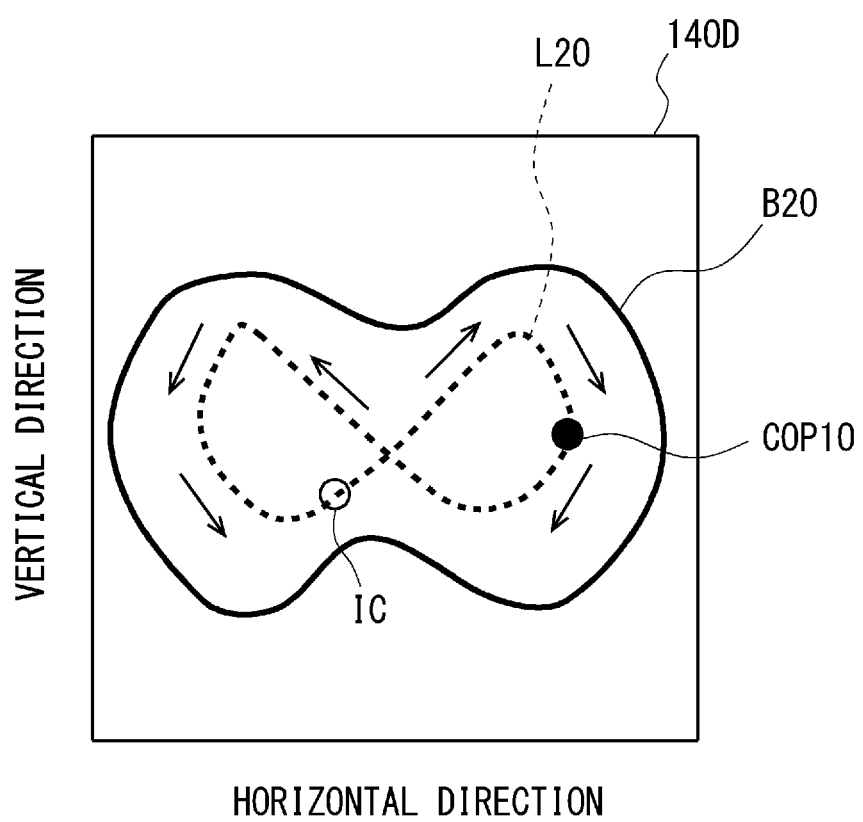
FIG. 13 shows a relationship between a transition of the center of gravity of a trainee and the threshold.

FIG. 13 shows a relationship between a transition of the center of gravity COP 10 of the trainee 900 and a threshold. An image 140D shown in FIG. 13 is obtained by extracting an area of the center of gravity COP 10 estimated from the skeleton model 900M. A dotted line L20 included in the image 140D shows a trajectory of the center of gravity COP 10 during walking training in a normal state. The center of gravity COP 10 is shifted in the shape of the letter 8 along the arrow on the dotted line L20. A point IC is included in the dotted line L20. The point IC corresponds to a position of 0% of the walking cycle shown in FIG. 4.

A line B20 drawn by the solid line surrounding the dotted line L20 indicates a threshold between the normal state and the abnormal state. That is, when the center of gravity COP 10 is moving in the area surrounded by the line B20, the state estimation unit 210c estimates the training performed by the trainee 900 to be the normal state. On the other hand, when the center of gravity COP 10 comes out from the area surrounded by the line B20, the state estimation unit 210c estimates the training performed by the trainee 900 to be the abnormal state.

Figure 14:
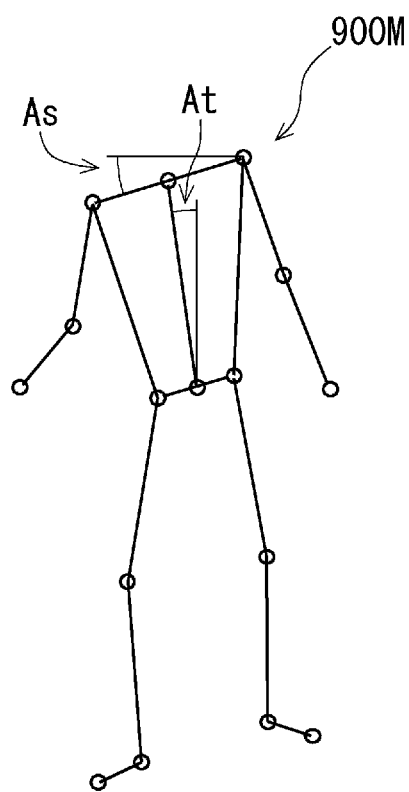
FIG. 14 shows a second example of a threshold set from image data.

Next, another example of processing using the skeleton model 900M will be described. FIG. 14 shows a second example of a threshold set from the image data. The skeleton model 900M shown in FIG. 14 is generated from an image of the trainee 900 during walking training. FIG. 14 shows an angle As formed by a line connecting the left and right shoulders of the skeleton model 900M and a line extending in the horizontal direction of the drawing, and an angle At formed by a midline and a line extending in the vertical direction of the drawing. The threshold setting unit 210a can use the angle As or the angle At as a threshold. In this case, the state estimation unit 210c calculates a value of the angle As or a value of the angle At during training from the skeleton model 900M, and estimates whether the training is in a normal state or an abnormal state from the calculated value.

For example, the threshold setting unit 210a can set an abnormal state when the angle At exceeds 20 degrees as a threshold. When the trainee 900 loses his/her balance in walking training, the angle At may exceed 20 degrees. In such a case, the state estimation unit 210c estimates that the training is in the abnormal state.

The threshold setting unit 210a may set an angular velocity or angular acceleration of the angle As or the angle At as a threshold. In this case, the state estimation unit 210c can estimate that the training is in the abnormal state when a change of the trainee 900's trunk is sudden, regardless of the posture of the trainee 900.

The above-described example of the skeleton model 900M is merely an example. That is, the parameters for setting the threshold and estimating the state are not limited to those described above. For example, parameters for setting the threshold and estimating the state may be acquired from a stride amount of the trainee 900's leg in a walking motion of the trainee 900. Further, the camera 140 for capturing the image of the trainee 900 is not necessarily provided in front of the trainee 900, and the image of the trainee 900 may be captured from the side or oblique direction of the trainee 900. Further, a plurality of cameras 140 may be installed to set thresholds or the like from a plurality of pieces of image data acquired by capturing images of the trainee 900. The output of the posture sensor 217, the front pulling unit 135, the rear pulling unit 137, or the load sensor 222 may be used as a parameter for setting the threshold or estimating the state.

The first embodiment has been described above. According to the first embodiment, it is possible to provide a walking training apparatus, a state estimation program, and the like for preventing lowering of the trainee's safety.

Second Embodiment

Figure 15:
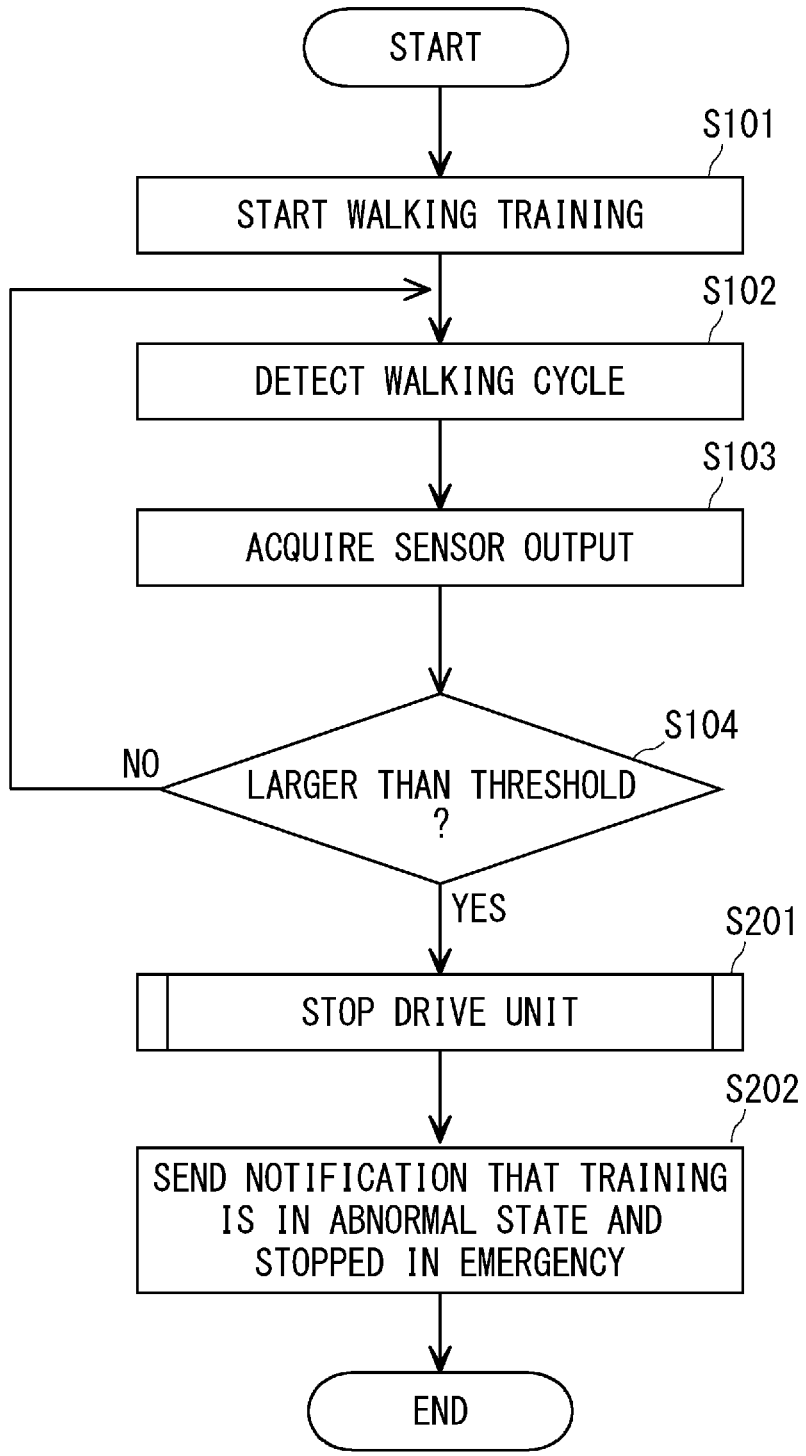
FIG. 15 is a flowchart showing processing of a walking training apparatus according to a second embodiment.

Next, a second embodiment will be described with reference to FIG. 15. In the second embodiment, processing after estimating the abnormal state differs from the processing according to the first embodiment shown in FIG. 8. FIG. 15 is a flowchart showing processing of the walking training apparatus according to the second embodiment. Hereinafter, the processing according to this embodiment will be described, while the description of processing the same as that of the processing according to the first embodiment is omitted.

When it is estimated in step S104 that the training being performed is in the abnormal state (step S104: YES), the overall control unit 210 performs processing for stopping the drive unit (step S201). The drive unit is a drive unit driven according to the trainee's motion in order to support the trainee's motion. The drive unit is, for example, the treadmill 131, the front pulling unit 135, the rear pulling unit 137, and the motor 121M.

In step S201, the overall control unit 210 performs processing in consideration of the trainee 900's physical safety. For example, when the drive unit is stopped, the overall control unit 210 decelerates the drive unit. Thus, the walking training apparatus 100 can effectively prevent a sudden load to be applied on the trainee 900.

Further, the overall control unit 210 may stop the drive unit after driving the drive unit in the reverse direction. For example, the overall control unit 210 drives the treadmill 131 in the reverse direction by several tens of centimeters. By performing such a process, the walking training apparatus 100 can bring the trainee 900 close to a predetermined initial position, for example, when the trainee 900 falls down and is moved along the treadmill 131. That is, the walking training apparatus 100 can stop the drive unit in a state where no load is applied to the trainee 900's body, and can easily resume the training. That is, with such a configuration, the walking training apparatus 100 can further effectively prevent lowering of the trainee's safety.

Next, the overall control unit 210 performs processing for notifying the trainee 900 and the training staff member 901 that the training has been stopped in an emergency due to an abnormal state (step S202). The processing for notifying that the training is in the abnormal state and has been stopped in an emergency may be displayed on the training monitor 138 or the management monitor 139, or may be achieved by means such as emitting a sound or light.

The second embodiment has been described above. In the second embodiment, processing for appropriately using the warning processing described in the first embodiment and the emergency stop processing shown in the second embodiment may be employed. That is, the walking training apparatus 100 according to the second embodiment has a threshold for executing the warning processing and a threshold for executing the emergency stop processing, and such processing may be executed in accordance with the training state.

According to the above-described configuration, the walking training apparatus 100 can automatically perform processing that must be operated by the training staff member 901 instantly. Thus, according to the second embodiment, it is possible to provide a walking training apparatus or the like that can reduce the load on the training staff member and that effectively prevents lowering of the trainee's safety.

Third Embodiment

Figure 16:
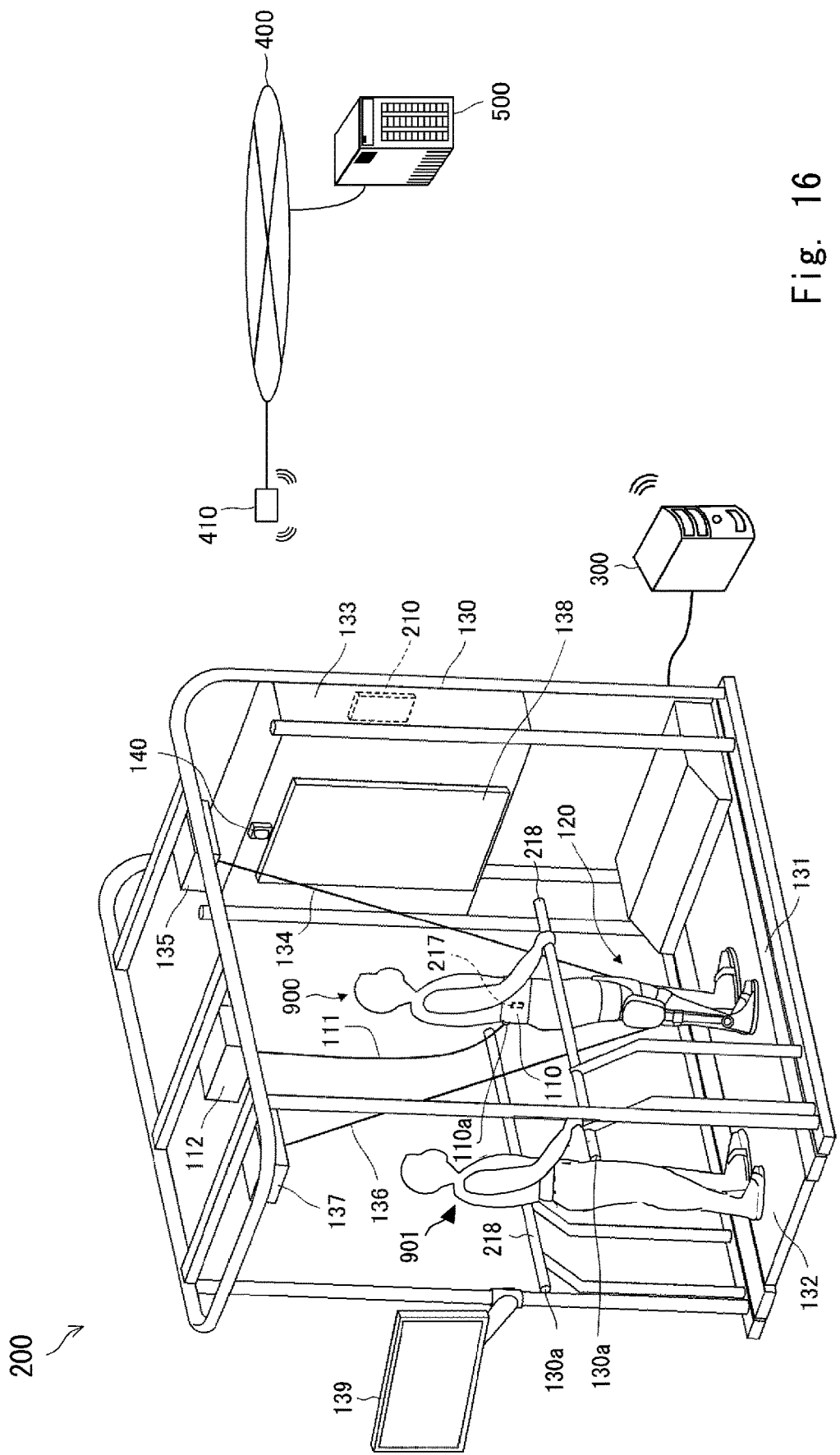
FIG. 16 is a schematic perspective view of a walking training apparatus according to a third embodiment.

Next, a third embodiment will be described. A rehabilitation support system according to the third embodiment differs from the rehabilitation support system according to the first embodiment in that in the rehabilitation support system according to the third embodiment, a state of training is estimated using a trained model stored in a server connected to the walking training apparatus. FIG. 16 is a general conceptual diagram showing an example of a configuration of the rehabilitation support system according to the third embodiment. The rehabilitation support system (rehabilitation system) according to the third embodiment mainly includes a walking training apparatus 200, an external communication apparatus 300, and a server (server apparatus) 500.

A hardware configuration of the walking training apparatus 200 differs from that of the walking training apparatus 100 according to the first embodiment in that the walking training apparatus 200 is communicably connected to the external communication apparatus 300. Note that a description for the part of the walking training apparatus 200 the same as a corresponding part of the walking training apparatus 100 according to the first embodiment will be omitted.

The external communication apparatus 300 is a specific example of transmission means for transmitting the profile data and rehabilitation data to the outside. The external communication apparatus 300 can have a function of receiving data output from the walking training apparatus 200 and temporarily storing the data, and a function of transmitting the stored data to the server 500.

The external communication apparatus 300 is connected to the control panel 133 of the walking training apparatus 200 by, for example, a USB (Universal Serial Bus) cable. The external communication apparatus 300 is connected to a network 400 such as the Internet or an intranet via a wireless communication device 410 by, for example, a wireless LAN (Local Area Network). Note that the walking training apparatus 200 may include a communication apparatus in place of the external communication apparatus 300.

The server 500 is a specific example of information processing means for receiving the profile data and processing the received profile data. The server 500 is connected to the network 400 and has a function of storing the profile data received from the external communication apparatus 300. The functions of the server 500 will be described later.

Figure 17:
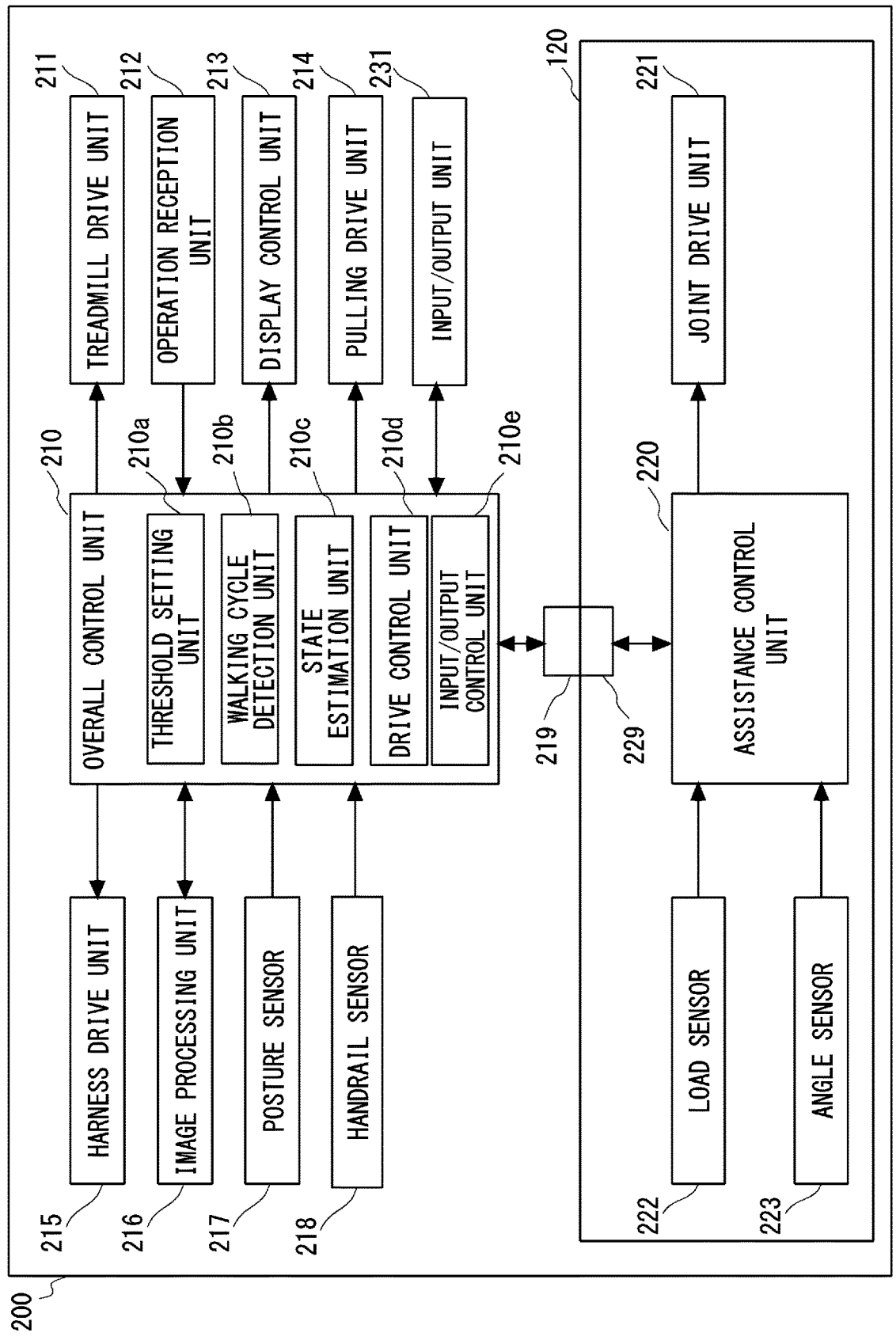
FIG. 17 is a block diagram showing a system configuration of the walking training apparatus according to the third embodiment.

Next, an example of the system configuration of the walking training apparatus 200 will be described with reference to FIG. 17. FIG. 17 is a block diagram showing an example of the system configuration of the walking training apparatus 200. The walking training apparatus 200 differs from the walking training apparatus 100 according to the first embodiment in that the walking training apparatus 200 includes an input and output unit 231.

The input and output unit 231 includes, for example, a USB (Universal Serial Bus) interface, and is a communication interface for connecting to an external device (external communication apparatus 300 or other external device). The input and output control unit 210e of the overall control unit 210 communicates with the external device through the input and output unit 231, rewrites the above-described control program in the overall control unit 210 and a control program in the assistance control unit 220, accepts commands, and outputs predetermined data.

With the above configuration, the walking training apparatus 200 communicates with the server 500 through the input and output unit 231 and the external communication apparatus 300 under the control of the input and output control unit 210e. For example, the input and output control unit 210e transmits sensor output data that is data of an output acquired from the sensor to the server 500 through the input and output unit 231 and the external communication apparatus 300. The input and output control unit 210e receives a state estimation signal indicating an estimation of a state of training corresponding to the transmitted sensor output data.

Next, the server 500 will be described in detail. The server 500 receives the sensor output data from the walking training apparatus 200 through the network 400 and then processes the received sensor output data. The server 500 uses the trained model to estimate a state of training from the received sensor output data. The trained model is generated by performing machine learning using a plurality of teacher data pieces. The server 500 uses the trained model to determine a recommended assistance level from the received sensor output data. The server 500 transmits a result of the estimation to the walking training apparatus 200 through the network 400. The server 500 may be configured to receive a plurality of sensor output data pieces from a plurality of walking training apparatuses 200. This allows the server 500 to collect the sensor output data.

Figure 18:
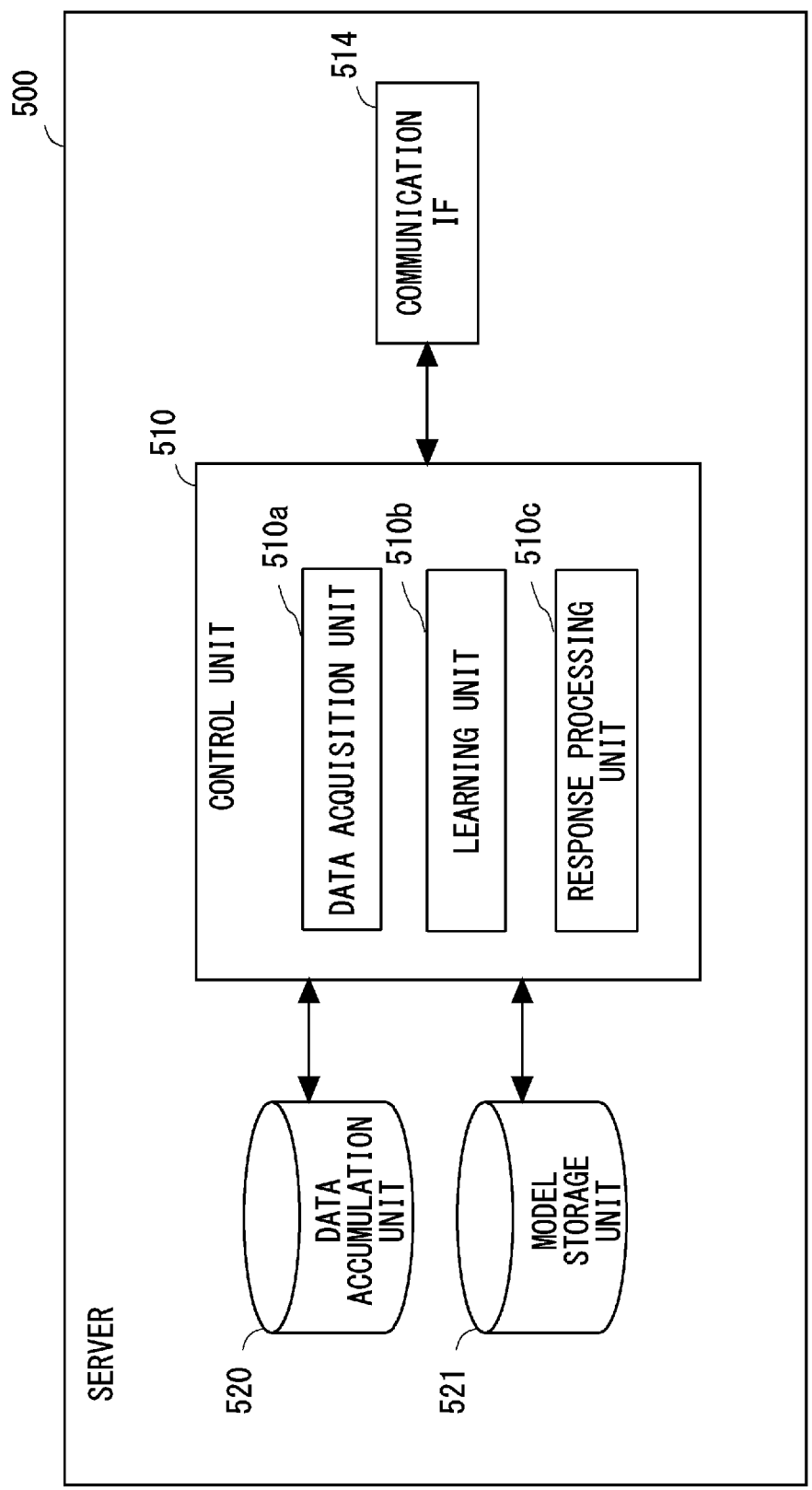
FIG. 18 is a block diagram showing an example of a learning model.

FIG. 18 is a block diagram showing an example of a configuration of the server 500. As shown in FIG. 18, the server 500 may include a control unit 510, a communication IF 514, a data accumulation unit 520, and a model storage unit 521. The control unit 510 is, for example, an MPU and controls the server 500 by executing a control program loaded from a system memory. The control unit 510 may include a data acquisition unit 510a, a learning unit 510b, and a response processing unit 510c, which will be described later. Further, in this case, the above-described control program includes a program(s) for implementing the functions of the aforementioned units 510a to 510c.

The communication IF 514 includes, for example, a wired LAN interface and is a communication interface for connecting to the network 400. The control unit 510 can receive sensor output data from the walking training apparatus 200 and transmit a processing result to the walking training apparatus 200 through the communication IF 514.

The data accumulation unit 520 includes a storage device such as an HDD or an SSD and stores the sensor output data and the like supplied from the walking training apparatus 200. The control unit 510 writes the sensor output data received from the external communication apparatus 300 into the data accumulation unit 520 through the communication IF 514.

Similarly, the model storage unit 521 includes a storage device such as an HDD or an SSD. Note that the data accumulation unit 520 and the model storage unit 521 may include (i.e., share) a common storage device. When the server 500 performs a rehabilitation support process in cooperation with the walking training apparatus 200, at least an operable trained model is stored in the model storage unit 521.

The server 500 has a function as a learning apparatus for generating a trained model in addition to a function for outputting a state estimation signal for estimating the state of the training for the sensor output data received from the walking training apparatus 200. That is, the control unit 510 may be configured so as to perform control to switch between a function as a learning apparatus and a function for performing a rehabilitation support process by using a trained model. However, the server 500 may be distributed to (or divided into) an apparatus that is used in a learning stage and an apparatus that is used in an operation stage in which a trained model is used.

In the learning stage, the data acquisition unit 510a acquires the sensor output data for acquiring a state estimation signal and a state label signal supplied corresponding to the sensor output data. The state label signal is generated in advance corresponding to the sensor output data in order to generate a trained model. For example, when the sensor output data acquired by the data acquisition unit 510a is output during training in a normal state, a state label corresponding to this case is a signal indicating a normal state. The data acquisition unit 510a acquires arbitrary sensor output data when the rehabilitation support process is performed.

The learning unit 510b is provided to make the server 500 function as a learning apparatus, and the response processing unit 510c is provided to make the server 500 execute a part of the rehabilitation support processing.

The model storage unit 521 stores at least one of a learning model that has not been trained yet (including those under training) (hereinafter referred to as an untrained model) and a learning model that has been already trained (hereinafter referred to as a trained model). The server 500 serving as the learning apparatus is a processing apparatus for processing various data. For example, the server 500 performs machine learning using the acquired sensor output data and teacher data to generate a trained model. The learning apparatus may be referred to as a learning model generating apparatus. When the server 500 functions as a learning apparatus, at least an untrained model is stored in the model storage unit 521.

(Learning Stage)

Figure 19:
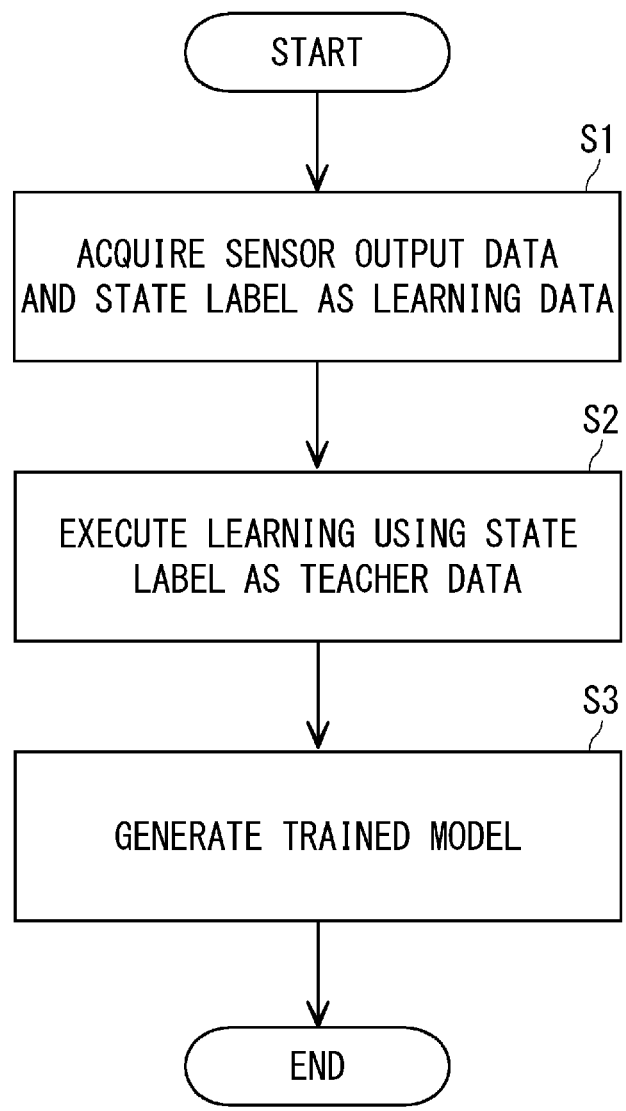
FIG. 19 is a flowchart showing an example of processing performed by a learning apparatus.

Next, the processing in the learning stage performed by the server 500 as the learning apparatus will be described with reference to FIG. 19. FIG. 19 is a flowchart for describing processing in the server 500, which is a learning apparatus.

First, the data acquisition unit 510a of the server 500 acquires the sensor output data and a state label as learning data (step S1). That is, when the server 500 performs learning, the sensor output data and the state label corresponding to the acquired sensor output data becomes one set of learning data.

Next, the learning unit 510b of the server 500 applies the acquired sensor output data to an input layer, and executes learning with the corresponding selected assistance level as the teacher data (step S2).

The data input to the learning apparatus includes a plurality of parameters applied to the input layer and the teacher data applied to the output layer. By performing the learning using such a plurality of data sets, the server 500, which is a learning apparatus, causes the learning unit 510b to learn. By using the above-mentioned learning data, the learning unit 510*b* learns to estimate the state of the training when the trainee uses the walking training apparatus 200.

Note that the type of the learning model to be trained and its algorithm are not limited to any particular types and algorithms. However, a neural network can be used as the algorithm and, in particular, a deep neural network (DNN) using multiple hidden layers may be used. As the DNN, for example, a feedforward (forward propagation type) neural network such as a multilayer perceptron (MLP) employing an error back propagation method can be used.

Next, the learning unit 510*b* generates a trained model updated by the performed learning (step S3). The trained model indicates a learning model at a stage where the learning model updated by the above processing becomes operable. By the above processing, the server 500 as the learning apparatus generates a trained model for outputting the state estimation signal. Then, the rehabilitation support system can estimate a state of the walking training by using the generated trained model.

The learning unit 510*b* may use a neural network having a recursive structure such as RNN (Recurrent Neural Network) as the learning model in addition to the above-described configuration. The RNN may also be a neural network (sometimes simply referred to as LSTM) extended to include LSTM (Long short-term memory) blocks.

(Operation Stage)

Figure 20:
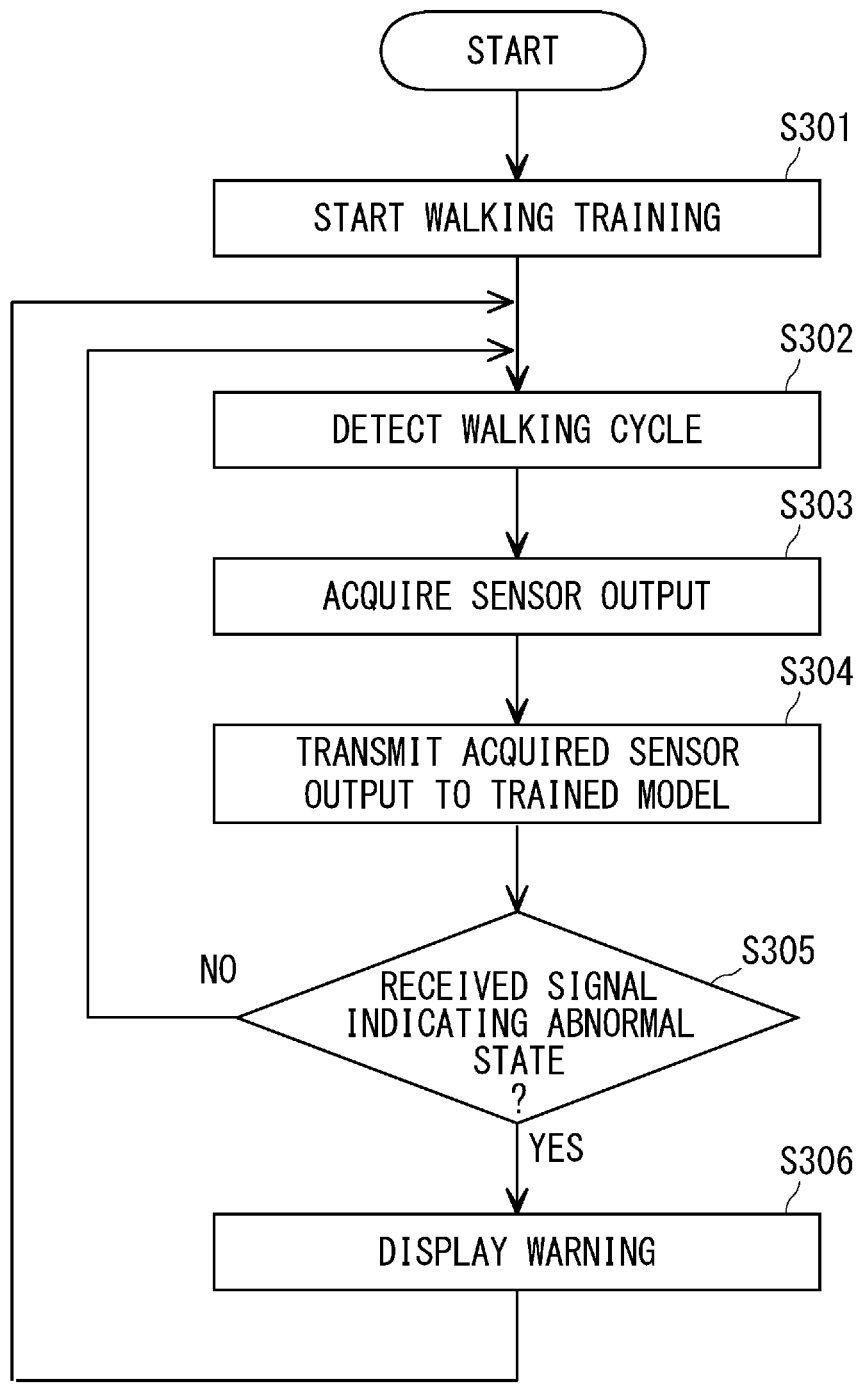
FIG. 20 is a flowchart showing processing of the walking training apparatus according to the third embodiment.

Next, processing performed by the walking training apparatus 200 in the operation stage will be described with reference to FIG. 20. An operation stage is a stage in which rehabilitation is performed using the trained model generated by the learning apparatus. FIG. 20 is a flowchart for explaining an example of the processing of the server. As described above, the walking training apparatus 200 can use the trained model by accessing the server 500. At the operation stage, mainly the walking training apparatus 200 and the server 500 connected to the walking training apparatus through a network cooperate with each other as a rehabilitation support system, and rehabilitation support processing is performed. First, the walking training apparatus 200 performs a process of starting walking training (step S301). Next, the walking training apparatus 200 detects a walking cycle (step S302), and acquires a sensor output corresponding to the detected walking cycle (step S303).

Next, the walking training apparatus 200 transmits the acquired sensor output to the trained model of the server 500 (step S304). When the walking training apparatus 200 transmits the sensor output to the server 500, the server 500 estimates a state of training being performed from the received sensor output, and transmits a state estimation signal to the walking training apparatus 200.

Next, the walking training apparatus 200 determines whether a signal indicating an abnormal state has been received from the server 500 (step S305). When it is not determined that the signal indicating an abnormal state has been received from the server 500 (step S305: NO), the walking training apparatus 200 returns to step S302 to detect the walking cycle again.

On the other hand, when it is determined that a signal indicating an abnormal state has been received from the server 500 (step S305: YES), the walking training apparatus 200 issues a warning (step S306). The warning process performed here is the same as that described in the first embodiment. Thus, the description of the warning process is omitted here. Next, the walking training apparatus 200 returns to step S302 to detect the walking cycle again.

Although the third embodiment has been described above, the third embodiment is not limited to the above-described configuration. The data set of the learning data may include the profile data of the trainee. By including the profile data of the trainee, the trained model can set a threshold suitable for each trainee. The process shown in FIG. 20 may be configured to stop in an emergency in case of an abnormal state, in a manner similar to the second embodiment.

In the third embodiment, the sensor output to be input to the learning model may be a plurality of sensor outputs. Further, the sensor output may be the image data itself. Further, the profile data of the trainee is not limited to the score data as described in the first embodiment, and instead may be qualitative data such as symptom information of a disease affected by the trainee or data indicating an attribute.

By such processing, the walking training apparatus 100 can display the received profile data and the state estimation signal corresponding to the state label. The PT can set the displayed recommended assistance level as an assistance level to be applied by the walking assistance apparatus 120. With such a configuration, the walking training apparatus 100 can appropriately set the assistance level regardless of the experience or intuition of the PT.

The third embodiment has been described so far. According to the third embodiment, it is possible to provide a trained model or the like that effectively prevents lowering of a trainee's safety.

The above-described program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (Read Only Memory), CD-R, CD-R/W, and semiconductor memories (such as mask ROM, PROM (Programmable ROM), EPROM (Erasable PROM), flash ROM, RAM (Random Access Memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

The present disclosure is not limited to the above-described embodiments, and can be appropriately changed without departing from the scope thereof. For example, the above-described walking training apparatus may be an apparatus that trains motions of the trainee's hip joint or ankle in addition to or instead of a motion of the trainee's knee joint. Further, the above walking training apparatus may be applied to a rehabilitation support apparatus or a rehabilitation support system that trains a motion of the trainee's arm.

From the disclosure thus described, it will be obvious that the embodiments of the disclosure may be varied in many ways. Such variations are not to be regarded as a departure from the spirit and scope of the disclosure, and all such modified examples as would be obvious to one skilled in the art are intended for inclusion within the scope of the following claims.

What is claimed is:

1. A non-transitory computer readable medium storing a state estimation program that causes a computer to function to determine a state of training in a rehabilitation support system used by a trainee to perform training of a preset motion, the state estimation program comprising:

acquiring a sensor output, the sensor output being an output of a sensor included in the rehabilitation support system in the training performed by the trainee;

setting a threshold for determining one of a normal state and an abnormal state of the training by multiplying a value calculated from the sensor output by a predetermined coefficient; and estimating whether the training is performed in the normal state or the abnormal state based on whether the output of the sensor does or does not deviate from the threshold, wherein the sensor output comprises data of a knee extension angle related to a walking cycle of the trainee, and the threshold is set on a upper limit and a lower limit of the knee extension angle corresponding to the walking cycle.

2. The non-transitory computer readable medium storing the state estimation program according to claim 1, wherein the acquiring further comprises acquiring profile data of the trainee in addition to the sensor output and the setting further comprises setting the threshold based on the sensor output and the profile data.

3. The non-transitory computer readable medium storing the state estimation program according to Claim 1, wherein the output of the sensor further comprises data acquired by detecting a walking posture of the trainee.

4. A rehabilitation support system comprising:

a drive unit configured to be driven to correspond to a motion of a trainee in order to support the motion of the trainee;

a sensor configured to detect at least one of a state of the trainee and a state of the drive unit;

an estimation unit configured to include the state estimation program according to claim 1 and to estimate whether the training performed by the trainee is in the normal state or the abnormal state by acquiring the sensor output; and an information presentation unit configured to present whether the training is in the abnormal state to the trainee or a training staff member assisting the trainee based on an estimation of the estimation unit.

5. The rehabilitation support system according to claim 4, further comprising:

a drive control unit configured to control the drive unit, wherein the drive control unit is configured to stop operation of the drive unit when the training is estimated to be in the abnormal state.

6. The rehabilitation support system according to claim 5, wherein the drive control unit is configured to, when the coperation of the drive unit is stopped, decelerate a driving speed of the drive unit and then stop the coperation of the drive unit.

7. The rehabilitation support system according to claim 5, wherein the drive control unit is configured to stop the operation of the drive unit and then operates the drive unit in a direction opposite to a driving direction immediately before the drive unit is stopped.

8. A rehabilitation support system comprising:

a drive unit configured to be driven to correspond to a motion of a trainee in order to support the motion of the trainee;

a sensor configured to detect at least one of a state of the trainee and a state of the drive unit;

a calculation unit configured to include a trained model, and to output a state estimation signal for estimating whether a training performed by the trainee is in a normal state or an abnormal state by acquiring a sensor output; and an information presentation unit configured to present whether the training is in the abnormal state to the trainee or a training staff member assisting the trainee based on the state estimation signal output provided by the calculation unit, wherein:

the training model is configured to cause a computer to function to determine a state of training in a rehabilitation support system used for the trainee to perform training of a preset motion, and the training model comprises an input layer configured to acquire the sensor output, the sensor output being an output of a sensor included in the rehabilitation support system, an intermediate layer configured to perform a calculation based on the sensor output acquired by the input layer, and an output layer configured to output a result of the calculation, and wherein:

the intermediate layer is learned by applying, to the output layer, an index indicating whether the training corresponding to the sensor output acquired by the input layer as learning data is in the normal state or the abnormal state as teacher data, and when the sensor output in the rehabilitation support system under training is input to the input layer, a state signal indicating whether the training is in the normal state or the abnormal state is output.

9. A state estimation method executed by a trained model stored in a non-transitory computer readable medium for determining a state of training in a rehabilitation support system used for a trainee to perform training of a preset motion, the state estimation method comprising:

acquiring a sensor output by the trained model, the sensor output being an output of a sensor included in the rehabilitation support system in the training performed by the trainee;

setting a threshold by the trained model for determining one of a normal state and an abnormal state of the training by multiplying a value calculated from the sensor output by a predetermined coefficient; and determining by the trained model whether the training is performed in the normal state or the abnormal state based on whether the output of the sensor does or does not deviate from the threshold, wherein the trained model is generated by performing machine learning;

the sensor output comprises data of a knee extension angle related to a walking cycle of the trainee, and the threshold is set on a upper limit and a lower limit of the knee extension angle corresponding to the walking cycle.

10. The state estimation method according to claim 9, wherein the trained model is a neural network model.

* * * * *